US006242210B1

(12) United States Patent
Björck et al.

(10) Patent No.: US 6,242,210 B1
(45) Date of Patent: Jun. 5, 2001

(54) TREATMENT OF BACTERIAL INFECTIONS

(75) Inventors: Lars Björck; Ulf Sjörbring, both of Lund (SE); Abdelhakim Ben Nasr, Cambridge (GB); Arne Olsén, Bjarred; Heiko Herwald, Malmo, both of (SE); Werner Müller-Esterl, Mainz (DE); Eva Mattsson, Lund (SE)

(73) Assignee: Actinova Limited (GB)

( * ) Notice: Subject to any disclaimer, the term of this patent is extended or adjusted under 35 U.S.C. 154(b) by 0 days.

(21) Appl. No.: 09/258,688

(22) Filed: Feb. 26, 1999

Related U.S. Application Data

(63) Continuation of application No. 09/194,098, filed as application No. PCT/SE97/00825 on May 20, 1997.

(51) Int. Cl.[7] .............................. C12Q 1/18; C12Q 1/14; C12Q 1/37
(52) U.S. Cl. ................. 435/32; 435/13; 435/36; 435/24; 435/244; 435/252.1; 435/252.8; 435/253.4; 435/848; 435/849; 435/851; 435/885; 435/882
(58) Field of Search .................... 435/32, 36, 24, 435/244, 252.1, 252.8, 253.4, 848, 849, 851, 885, 882, 13

(56) References Cited

U.S. PATENT DOCUMENTS

| | | | | |
|---|---|---|---|---|
| 4,693,993 | * | 9/1987 | Stewart et al. | 514/14 |
| 4,845,242 | | 7/1989 | Powers et al. | 549/283 |
| 4,985,354 | * | 1/1991 | Toyomaki et al. | 435/24 |
| 5,416,191 | * | 5/1995 | Cheronis et al. | 530/314 |
| 5,620,958 | * | 4/1997 | Cheronis et al. | 514/15 |
| 5,635,593 | * | 6/1997 | Cheronis et al. | 530/314 |

FOREIGN PATENT DOCUMENTS

WO 92/22320  12/1992  (WO).
WO 96/08569   3/1996  (WO).

OTHER PUBLICATIONS

Balis et al., "Efficacy of S–2441, a Synthetic Oligopeptide, in a Rat Model for Gram–Negative Bacteremia," *Circulatory Shock* 15:5–14, 1985.
Bao et al., "HOE 140, a New Highly Potent and Long–Acting Bradykinin Antagonist in Conscious Rats," *European Journal of Pharmacology* 200:179–182, 1991.
Ben Nasr et al., "Absorption of Kininogen from Human Plasma by *Streptococcus Pyogenes* is followed by the release of Bradykinin," *Biochem. J.* 326:657–660, 1997.
Ben Nasr et al., "Assembly of Human Contact Phase Proteins and Release of Bradykinin at the Surface of Curli–Expressing *Escherichia coli*," *Molecular Microbiology* 20(5):927–935, 1996.
Ben Nasr et al., "Human Kininogens Interact with M Protein, a Bacterial Surface Protein and Virulence Determinant," *Biochem. J.* 305:173–180, 1995.
Berge and Sjobring, "PAM, a Novel Plasminogen–Binding Protein from *Streptococcus Pyogenes*," *The Journal of Biological Chemistry* 268(34):25417–25424, 1993.
Fischetti, "Streptococcal M Protein: Molecular Design and Biological Behavior," *Clinical Microbiology Reviews* 2(3):285–314, 1989.

(List continued on next page.)

*Primary Examiner*—Louise N. Leary
(74) *Attorney, Agent, or Firm*—Seed IP Law Group

(57) ABSTRACT

An assay for compounds useful in the treatment of a bacterial induced coagulation disorder has the following steps:
  a) incubating a plasma sample with a strain of bacteria;
  b) adding a compound to be assayed to the plasma sample before, during or after step (a);
  c) conducting an activated partial thromboplastin time test;
  d) determining the clotting time.

5 Claims, 18 Drawing Sheets

OTHER PUBLICATIONS

Ghebrehiwet et al., "Mechanisms of Activation of the Classical Pathway of Complement by Hageman Factor Fragment," *J. Clin. Invest.* 71:1450–1456, 1983.

Herwald et al., "Activation of the Contact–Phase System on Bacterial Surfaces—a Clue to Serious Complications in Infectious Diseases," *Nature Medicine* 4(3):298–302, 1998.

Herwald et al., "Streptococcal Cysteine Proteinase Releases Kinins: a Novel Virulence Mechanism," *J. Exp. Med.* 184:665–673, 1996.

Lottenberg, "Contact Activation Proteins and the Bacterial Surface," *Trends in Microbiology* 4(11):413–415, 1996.

Maeda et al., "Role of Bradykinin in Microbial Infection: Enhancement of Septicemia by Microbial Proteases and Kinin," *Agents Actions Supplemental* 42:159–165, 1993.

Mak and Barnes, "Autoradiographic Visualization of Bradykinin Receptors in Human and Guinea Pig Lung," *European Journal of Pharmacology* 194:37–43, 1991.

Morrison and Cochrane, "Direct Evidence for Hageman Factor (Factor XII) Activation by Bacterial Lipopolysaccharides (Endotoxins)," *The Journal Of Experimental Medicine* 140:797–811, 1974.

Olsén et al., "Fibronectin Binding Mediated by a Novel Class Surface Organelles on *Escherichia coli*," *Nature* 338:652–655, 1989.

Pruneau et al., "Characterization of Bradykinin Receptors from Juvenile Pig Coronary Artery," *European Journal of Pharmacology* 297:53–60, 1996.

Sawutz et al., "Pharmacology and Structure–Activity Relationships of the Nonpeptide Bradykinin Reactor Antagonist WIN 64338," *Can. J. Physiol. Pharmacol.* 73:805–811, 1995.

Whalley and Cheronis, "Kinin Antagonists as Human Therapeutics," *Agents Actions Supplemental* 42:167–176, 1993.

Whalley et al., "CP–0127, A Novel Potent Bradykinin Antagonist, Increases Survival in Rat and Rabbit Models of Endotoxin Shock," *Agents Actions Supplemental* 38:413–420, 1992.

Wirth et al., "DesArg$^9$–D–Arg[Hyp$^3$,Thi$^5$,D–Tic$^7$, Oic$^8$]–bradykinin (desArg$^{10}$–[Hoel40])is a Potent Bradykinin B$_1$ Receptor Antagonist," *European J. Pharmacol.* 205:217–218, 1991.

Wirth et al., "Kinin Receptor Antagonists: Unique Probes in Basic and Clinical Research," *Can. J. Physiol. Pharmacol.* 73:797–804, 1995.

* cited by examiner

Bacterial concentration (cfu/ml)

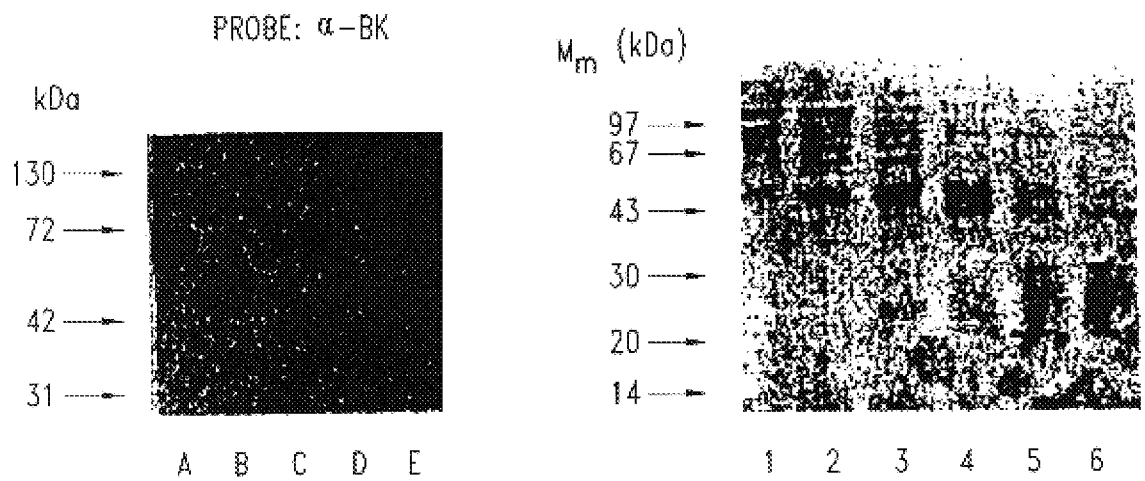
Fig. 14
Fig. 15
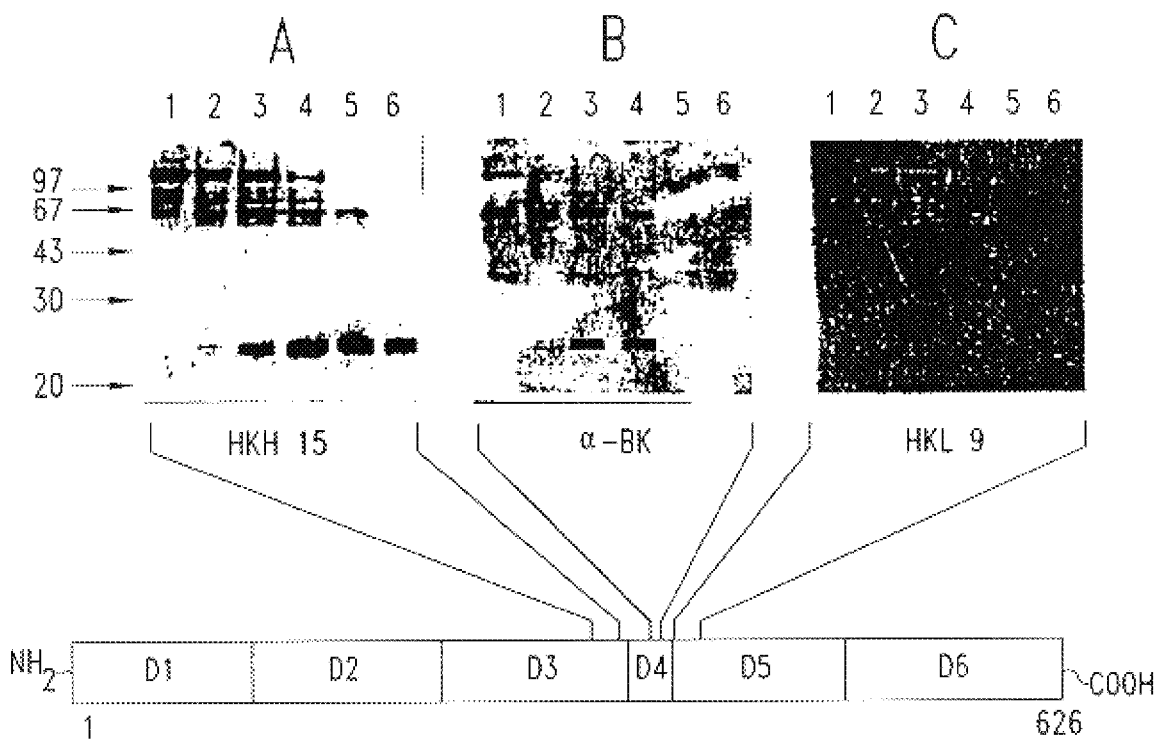
Fig. 16

TREATMENT OF BACTERIAL INFECTIONS

CROSS-REFERENCE TO RELATED APPLICATIONS

This application is a continuation-in-part of U.S. patent application Ser. No. 09/194,098, filed Jun. 25, 1999; which application is a 371 conversion of PCT Application No. PCT/SE97/00825, filed May 20, 1997.

TECHNICAL FIELD OF THE INVENTION

The invention relates to assays for the detection of compounds useful for the treatment of the bacterial infection and in particular conditions associated with infection by curli-expressing gram negative bacteria and streptococci.

BACKGROUND OF THE INVENTION

Some micro-organisms such as Streptococci, Salmonella, E.coli and S.aureus may cause severe invasive infections such as sepsis or septic shock. Fever, hypotension and bleeding disorders are common symptoms of sepsis and septic shock. Invasive infections caused by these bacteria may result from resistance to antibiotics or defects in the immune system of the infected individual.

The endogenous or intrinsic pathway of inflammation and coagulation is triggered by assembly of the contact phases system. The contact phase system is orchestrated by three serine proteases, factor XI (hereinafter referred to as F XI), factor XII (F XII) and plasma kallikrein (PK) as well as the non-enzymatic co-factor H-kininogen (HK). H-kininogen forms equimolar complexes with F XI and PK. The local activation of this proteolytic system triggers different cascades such as the surface-dependent activation of blood coagulation, fibrinolysis, kinin generation and inflammation reactions.

Events which allow the assembly of the contact phase components lead to conversion of F XII to the active enzyme F XIIa which triggers the contact phase system. Partially activated V XII cleaves PK which is bound to surfaces via HK. By a mechanism of reciprocal activation, PK amplifies the activity of F XII and in addition PK cleaves HK to release the nona peptide bradykinin. Activated F XII cleaves F XI into its active form which leads to initiation of the intrinsic pathway of coagulation.

Bradykinin and the physiologically important related peptides kallidin (Lys-bradykinin) and Met-Lys bradykinin, contract smooth muscle for example to produce diarrheoa and inflammatory bowel disease and asthma, lower blood pressure, mediate inflammation as in allergies, arthritis and asthma, participate in blood clotting and complement-mediated reaction in the body, mediate rhinitis (viral, allergic and non-allergic) and are over produced in pathological conditions such as acute pancreatitis, hereditary angioneurotic edema, post-gastrectomy dumping syndrome, carcinoid syndrome, anaphylactic shock, reduced sperm mobility and certain other conditions.

As a result of the fact that bradykinin is involved in all the above mentioned clinical indications, a large number of bradykinin antagonists have been developed. Such antagonists are disclosed in e.g. U.S. Pat. No. 4,693,993. Wirth et al., Can. J. Physiol. Pharmacol. Vol. 73 pp 797–804 presents clinical studies regarding administering bradykinin antagonists for treating post-operative pain, asthma, anaphylactoid reactions, systemic inflammatory response syndrome, and suspected sepsis, head injury and hantavirus infections. A review on clinical applications of bradykinin antagonists can be found in Cheronis et al. eds: Proteases, Protease Inhibitors and Protease Derived Peptides pp 167–176. Although these citations disclose administration of bradykinin antagonists for treating sepsis, it is evident that the suspected sepsis treated by said antagonists it not primarily caused by bacterial infections. Accordingly the citations are completely silent about using bradykinin antagonists for treating bacterial infections. Moreover it is evident that bradykinin antagonists have been administered to relieve the symptoms of inflammation.

SUMMARY OF THE INVENTION

Some of the symptoms of sepsis may be explained by activation of the contact phase system. However the precise mechanisms involved are not well understood. The inventors have now established the initial stages involved in activation of the contact phase system during bacterial infection. These studies have led to new assays being proposed to identify agents which specifically target the reactions resulting from bacterial activation of the contact phase system. These studies also demonstrate the disruption of the normal coagulation pathway in bacterial infections and thus propose new substances to treat conditions such as sepsis and septic shock.

The invention provides a number of assays to identify useful agents for the treatment of bacterial infections. In a first aspect, the invention provides an assay for compounds useful in the treatment of a bacterial-induced coagulation disorder, which assay comprises the steps of:

a) incubating a plasma sample with a strain of bacteria;

b) adding a compound to be assayed to the plasma sample before, during or after step a);

c) conducting an activated partial thromboplastin time aPTT test on the sample after steps a) and b);

d) determining the clotting time.

In a second aspect, the invention provides an assay for compounds useful in the treatment of a bacterial-induced coagulation or inflammatory disorder, which assay comprises the steps of:

a) incubating a strain of bacteria with one or more contact phase proteins selected from the group consisting of H-kininogen, prekallikrein, factor XII and factor XI;

b) adding a compound to be assay before, during or after step a); and c) determining the binding of the contact phase proteins to the bacterial surface.

In a further aspect, the invention provides an assay for compounds useful in the treatment of a bacterial induced coagulation or inflammatory disorder, which assay comprises the steps of:

a) incubating a strain of bacteria with one or more contact phase proteins selected from the group consisting of H-kininogen, prekallikrein, factor XII and factor XI b) adding the compound to be assayed before, during or after step a); and c) determining the activation of the or each contact phase protein.

By monitoring the interactions between bacteria and the contact phase components, agents can be identified which may be useful in the treatment of shock, sepsis and bleeding disorders seen in more severe bacterial infections.

or curli-deficient Ymel-1 (□) bacteria were incubated separately with 0.5–1 ng ($10^4$ cpm) H-kininogen (HK), L-kininogen (LK), prekallikrein (PK), factor XI (FXI), or factor XII (FXH); all proteins were from human plasma. Incubation for 60 min at 37° C. was followed by washing, centrifugation, and measuring of the radioactivity of the pellet. Binding was expressed as percentage of the total amount of [$^{125}$I]-labeled protein added to the bacteria. Mean values±SEM are indicated.

Figure 13:
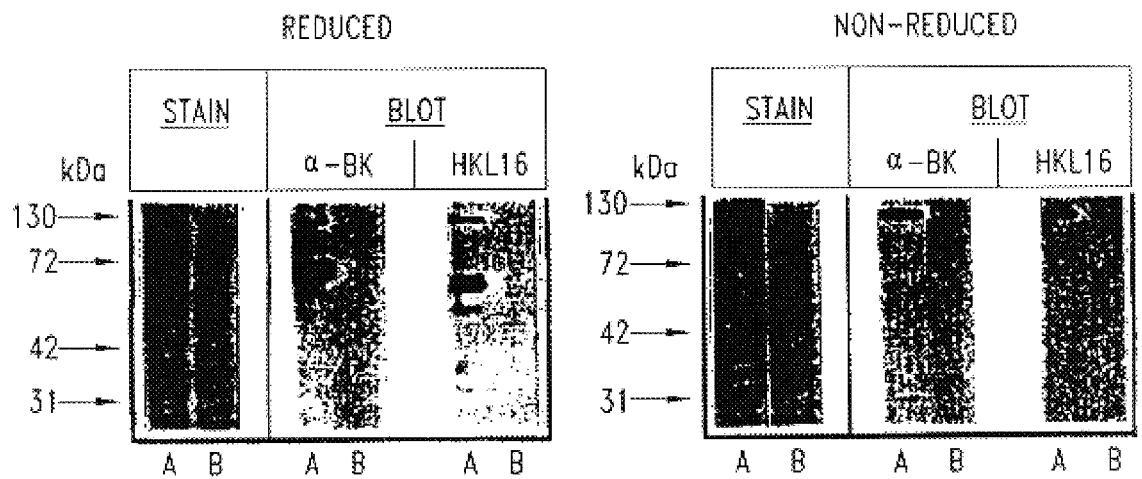
Figure 17A:
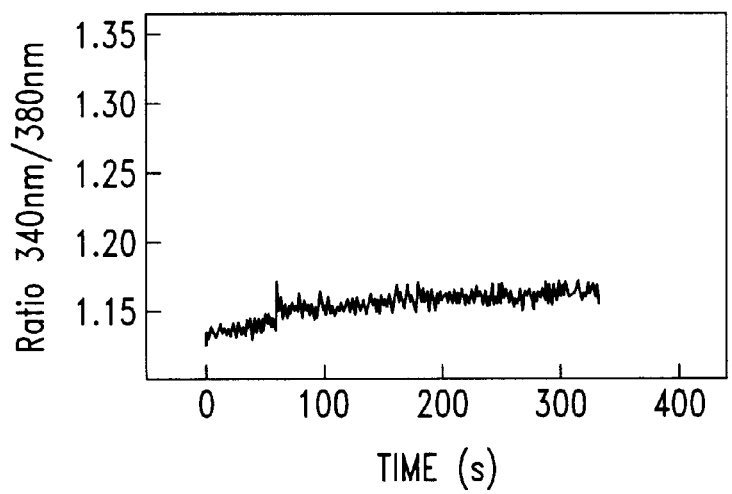
Figure 17B:
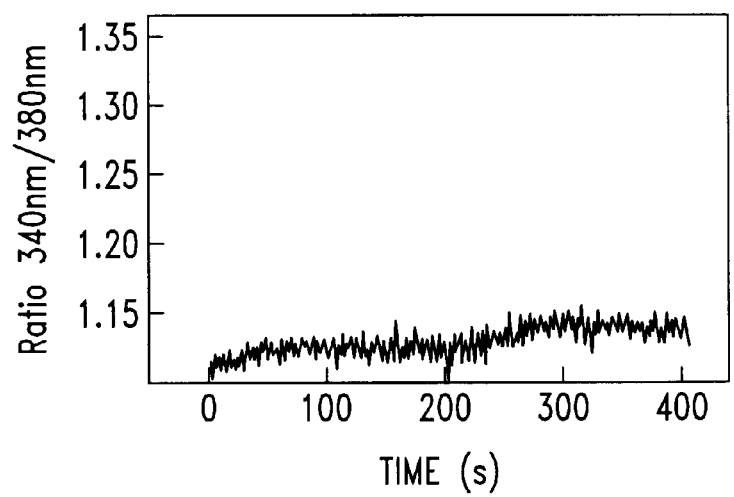
Figure 17C:
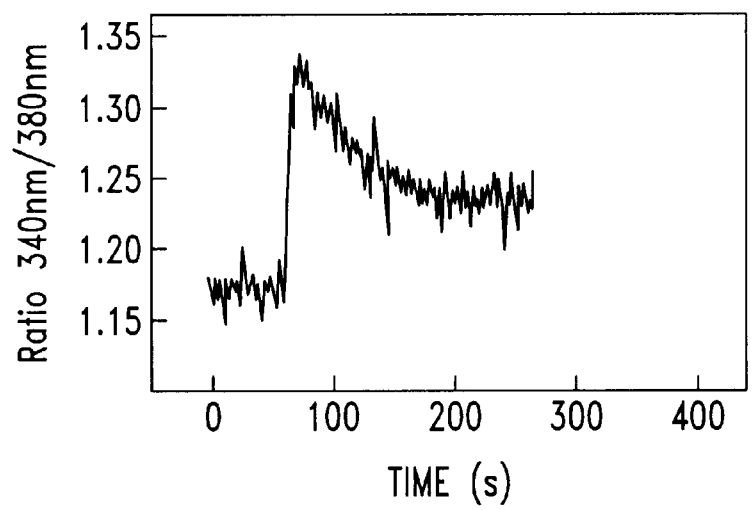
Figure 17D:
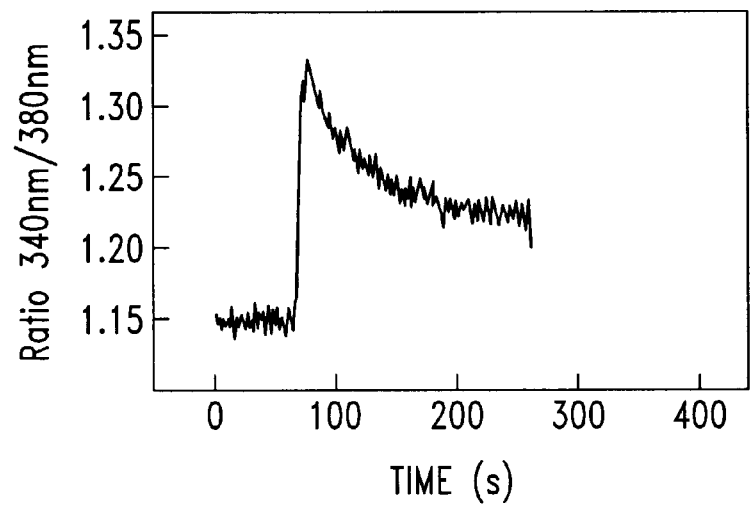

FIG. 13 shows that HK absorbed by and eluted from curliated E. coli is partially cleaved. Following incubation with human fresh plasma, proteins were eluted from curliated Ymel (A) or curli-deficient Ymel-1 (B) bacteria with pH 2.0, and subjected to SDS-PAGE (10%) under reducing or non-reducing conditions followed by staining with Coomassie Blue (STAIN). Replicas of these gels were probed with antibodies α-BK or HLK 16, followed by peroxidase-labeled secondary antibodies (BLOT).

FIG. 14 discloses that plasma killikrein cleaves surface-bound H-kininogen and releases bradykinin. Curliated Ymel bacteria were preincubated with human plasma, washed, and incubated with buffer alone for 40 min (A) or with activated plasma kallikrein (0. 1 mg/ml) for 5 min (B), 10 min (C), 20 min (D), and 40 min (E). Proteins bound to the bacteria were eluted with pH 2.0 and subjected to SDS-PAGE (10%), electroblotted onto a PVDF filter and probed with plyclonal antibodies against bradykinin (α-BK), followed by secondary peroxidase-labeled antibodies.

FIG. 15 relates to cleavage of H-kininogen by the streptococcal cysteine proteinase (SCP). H-kininogen (30 μg) was incubated with 0.07 μg of SCP (molar ratio of 100:1). After 15 min (lane 2), 30 min (3), 60 min (4), 120 min (5), or 180 min (6) of incubation aliquots of the reaction mixture (4 μg protein each) were separated by SDS-PAGE (10% v/v) under reducing conditions, followed by staining with Coomassie Brilliant Blue. For control H-kininogen incubated for 180 min in the absence of SCP was applied (lane 1). Note that a small amount of the purified H-kininogen exists in its kinin-free two chain form. Standard molecular marker proteins were run simultaneously (not shown); their relative positions are indicated on the left.

Figure 3:
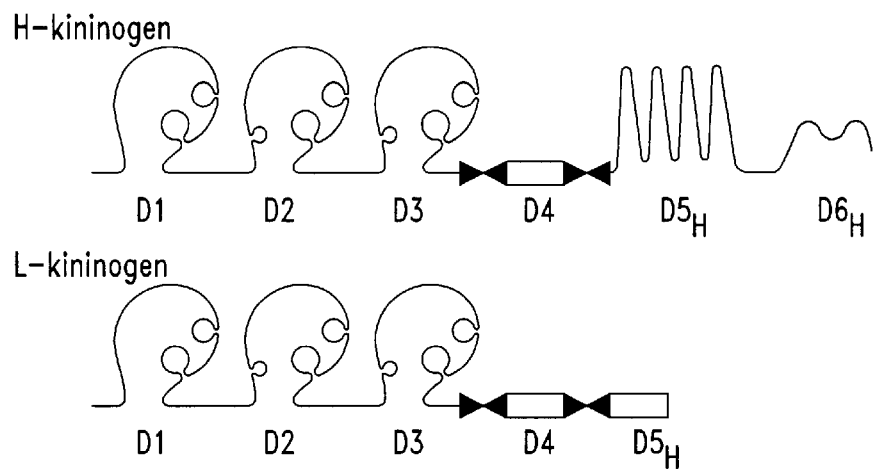
FIG. 3 discloses the gross structure of mammalian kininogens. H-kininogen and L-kininogen share their heavy chain domains, D 1 to D4, and differ in their light chain domains, $D5_H/D6_H$ and $D5_L$, respectively. Domains D I to D3 are of cystatin-like structure; domain D2 inhibits calpain and papain-like cystein proteinases whereas D3 inhibits only papain-like enzymes and exposes a cell-binding site. The kinin segment is located in domain D4. Domain $D5_H$ of H-kininogen exposes a high-affinity cell-binding site which is also used by streptococcal M protein. Domain $D6_H$ contains the overlapping binding sites for prekallikreinand factor XI. The function of $D5_L$ of L-kininogen is unknown. Protein-sensitive regions flanking the kinin segment are indicated by pairs of solid arrowheads.

FIG. 16 shows an immunoprint analysis of H-kininogen cleavage products. Aliquots from the reaction mixture of H-kininogen (30 μg) and SCP (0.07 μg) were removed after 15 min (lane 2), 30 min (3), 60 min (4), 120 min (5), or 180 min (6) and separated by SDS-PAGE followed by electrotransfer onto nitrocellulose. For control native H-kininogen incubated for 180 min in the absence of SCP (1) was applied. Blots were incubated with HKH 15 antibody (A), α-BK antibodies (B), or HKL 9 antibody (C). Bound antibodies were visualized with peroxidase labelled anti-mouse or anti-rabbit immunoglobulins and the chemiluminescence technqiue. The relative locations of the antibodies' target epitopes, are indicated on the bottom; the domain designation is that of FIG. 3. Note that α-BK shows a high affinity for kininogen fragments rather than for the uncleaved H-kininogen.

FIG. 17 discloses that $Ca^{2+}$ release from intracellular stores induced by H-kininogen cleavage products. Confluent human fibroblasts loaded with fura-2 were incubated with untreated H-kininogen (A), and H-kininogen cleaved by SCP for 30 min (B), 60 min (C), or 120 min (D) at 37° C. The intracellular $Ca^{2+}$ release was measured as the ratio of fluorescence at excitation wavelengths of 340 nm and 380 nm, respectively.

Figure 18:
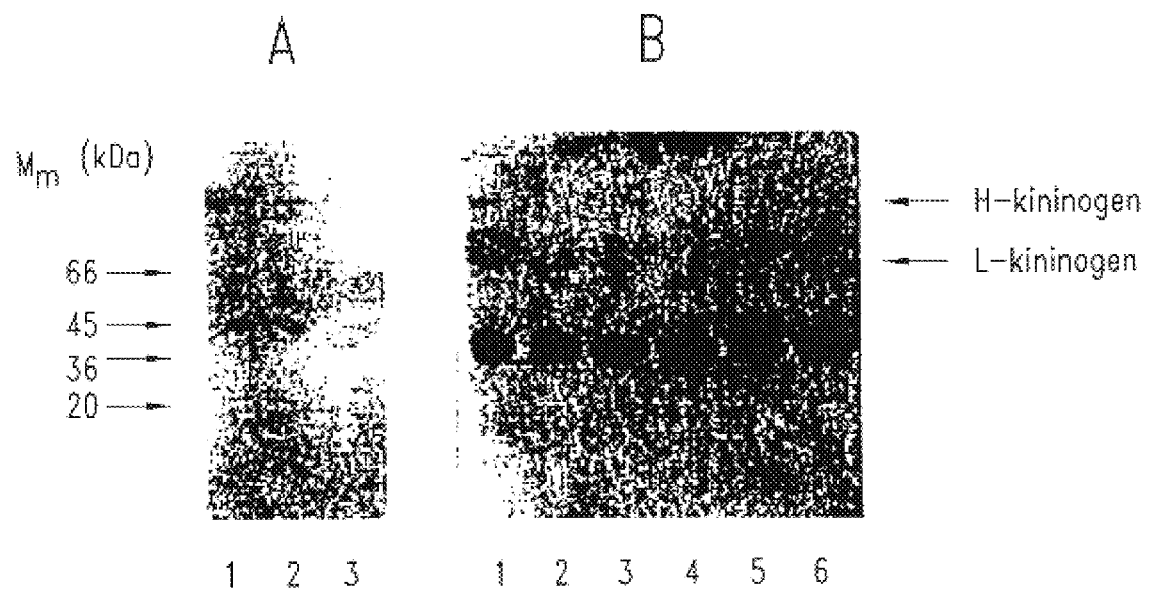

FIG. 18 relates to H-kininogen cleavage in plasma. Human plasma (100 μl) was incubated with 3.2 μg of SCP. Samples were taken after 15 min (lane 2), 30 min (3), 45 min (4), 60 min (5), or 90 min (6) of incubation and separated by SDS-PAGE followed by the transfer of the proteins onto nitrocellulose and immunostaining by antibodies against native H-kininogen (AS88; panel A) or to BK (α-BK; B). For control, plasma was incubated in the absence of SCP for 90 min (1). The relative positions of the human plasma kininogens are marked on the right.

Figure 19:
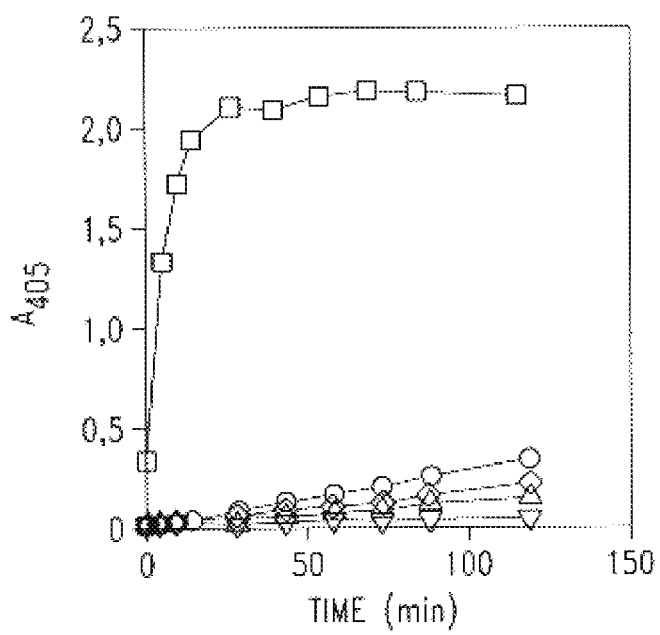

FIG. 19 shows the time course of prekallikrein activation by various proteinases. Plasma prekallikrein was incubated for 1 h with factor XII in a molar ratio of 100:1 (□) or with SCP in molar ratio of 100:1 (◊) ;and 10:1 (o). At the indicated time points aliquots of the reaction mixtures were removed, and their amidolytic activity tested by a chromogenic substrate assay (H-D-Pro-Phe-Arg-pNA). For control, prekallikrein incubated in the absence of SCP (Δ), or SCP alone (∇) were tested.

Figure 20:
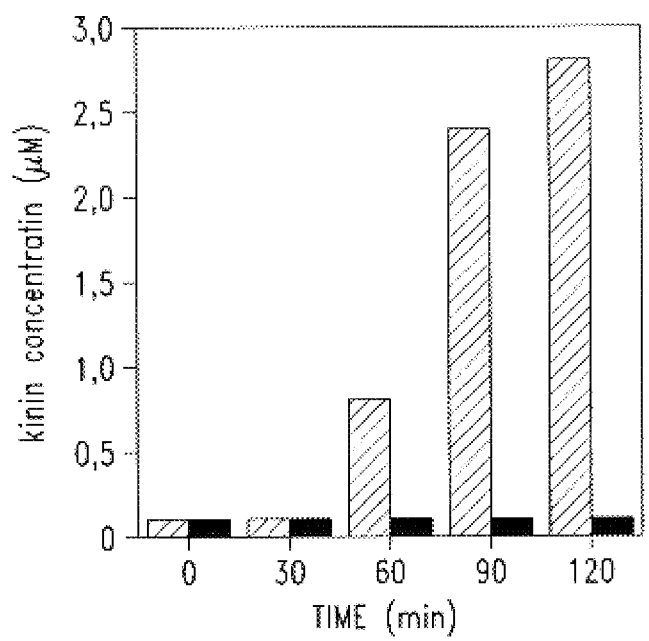

FIG. 20 discloses kinin generation by SCP in plasma followed by ELISA. Human plasma (100 μl) was incubated with 3.2 μg of SCP (■), aliquots of the reaction mixture were removed at the time points indicated, and assayed for their kinin concentration by a competitive ELISA. For control plasma was incubated under identical conditions except that SCP was omitted (■). Note that the lower detection limit for bradykinin is approximately $10^7$ mol/l of plasma.

Figure 21:
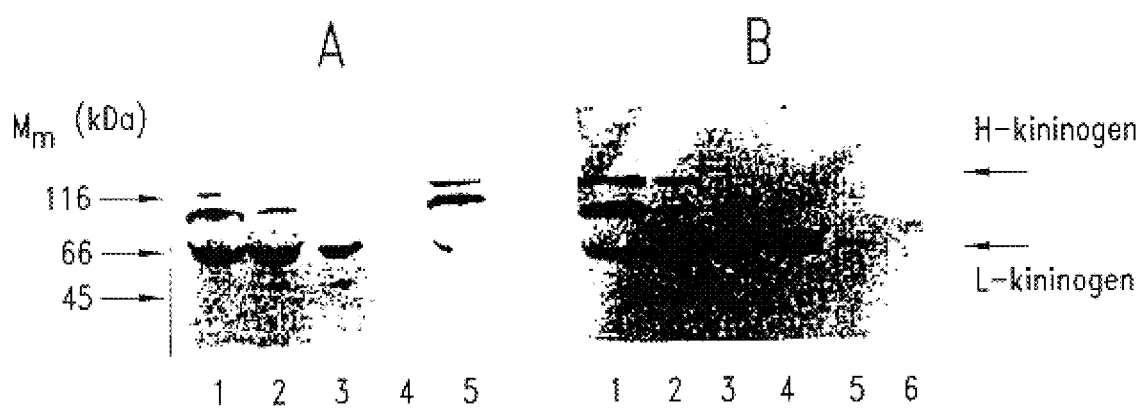

FIG. 21 shows cleavage of plasma kininogens by SCP in vivo. Panel A: Mice were injected i.p. with 0.5 mg of purified SCP. Plasma samples were drawn from the animals after 60 min (lane 2), 150 min (lane 3), and 300 min (lane 4). Alternatively, 0.5 mg SCP mixed with 0.2 mg Z-Leu-Val-Gly-$CHN_2$ was injected, and a plasma sample from this mouse was taken 300 min after injection (lane 5). For control, plasma from a mouse injected with PBS alone was used (lane 1). One 82 of each sample was separated by SDS-PAGE, transferred to nitrocellulose and immunostained with antibodies to bradykinin (α-BK). The relative positions of the market proteins are given to the left, and those of the mouse plasma kininogens are indicated to the right. Panel B: Mice were injected (i.p.) with PBS alone (lane 1), 0. 1 mg of SCP (lane 2), 0.2 mg of SCP (lane 3), 0.3 mg of SCP (lane 4), 0.4 mg of SCP (lane 5), or 0.5 mg of SCP (lane 6). Plasma samples were taken 300 min after injection.

Figure 22:
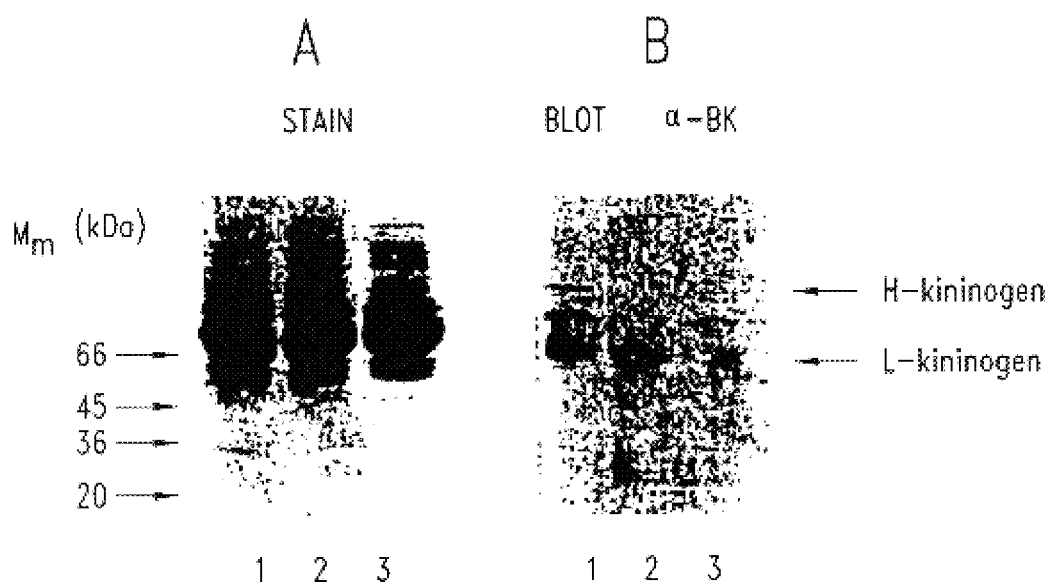

FIG. 22 relates to cleavage of plasma kininogens by S. pyogenes in vivo. Mice were injected i.p. with 0.5 mg of purified SCP or with living S. pyogenes bacteria ($3\times10^8$ cells) diluted in 0.5 ml PBS. A. Plasma samples (1 μl each) from animals injected with PBS alone (lane 1), with purified SCP (lane 2), or with S. pyogenes bacteria (lane 3) were run on SDS-PAGE and stained with Coomasie Brilliant Blue. B. An identical replica on nitrocellulose was probed with antibodies to bradykinin (α-BK). Standard molecular marker proteins were run simultaneously (not shown); their relative positions are indicated on the left. The positions of mouse kininogens are marked.

Figure 23:
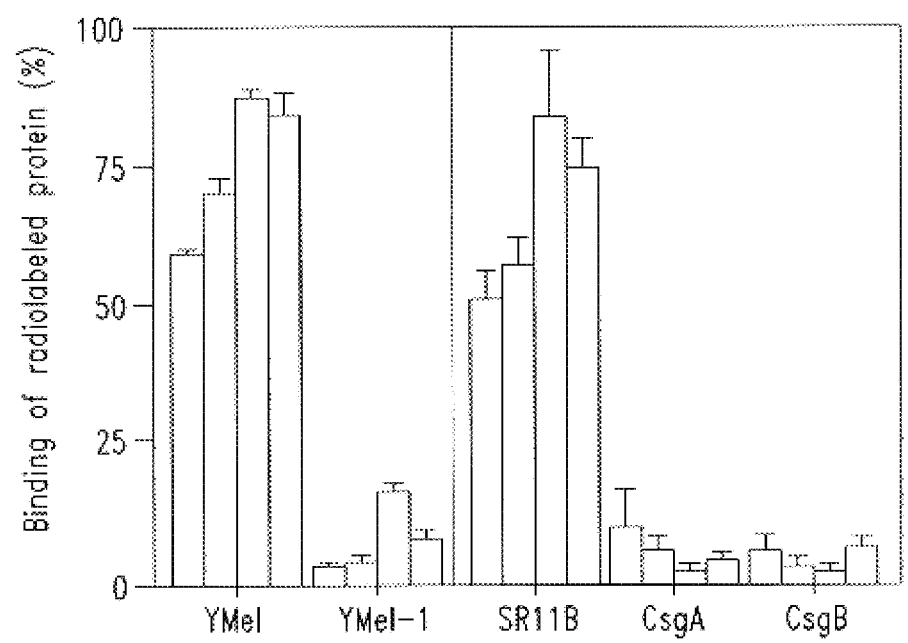
Figure 24A:
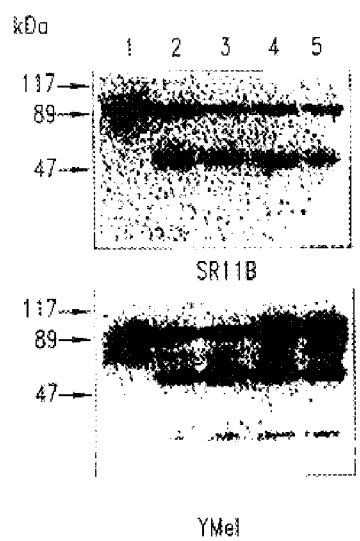

FIG. 23. Binding of radiolabelled contact phase proteins to curliated E.coli and S.typhimurium. [$^{125}$I]labelled F XI, F XII, PK or HK were incubated with suspensions of the bacterial strains YMel, YMel-1 from E.coli or SRIIB, CsgA, CsgB from S.typhimurium. Binding is expressed as the percentage of bound vs. total radioactivity. Data represents means±S.D. of 3 experiments each done in duplicate FIG. 24. A. Limited proteolysis of contact phase factor XII following incubation with S.typhimurium and E.coli. [$^{125}$I]labelled F XII (lane 1) was incubated with the bacterial strains SRIIB or YMel for 10 min (2), 15 mins (3), 30 min (4), and 45 min (5). Samples were run on SDS-PAGE under reducing conditions and visualized by autoradiography B and C. Activation of contact phase factors by *S.typhimurium* and *E.coli*. In B, [$^{125}$I]-PK was incubated for 10 min with SRIIB or YMel in the absence (−) or presence (+) of unabeled F XI, F XII and HK and centrifuged. The pellets were dissolved and run on SDS-PAGE under reducing conditions followed by autoradiography. In C, same as in B except that [$^{125}$I]-HK was used, and unlabeled PK but not HK was present in the incubation buffer.

FIG. 25. A. Generation of bradykinin at the bacterial surface. Human plasma was incubated with strains YMel, YMel-1, SRIIB, CsgA or CsgB. The amount of bradykinin (BK; pg/$10^{10}$ cells) present in the incubation mixtures was measured by a competitive radioimmunoassay. For control normal plasma (a) and plasma incubated in the absence of bacteria (b) were incubated. B. Effects of bacteria on the activated partial thromboplastin time (aPTT). Normal human plasma was pre-incubated for 30 sec with strains YMel, YMel-1, SRIIB, CsgA and CsgB. The clotting was initiated by adding kaoline and $CaCl_2$. For control plasma was incubated with vehicle alone. The dose dependent effect of YMel on aPTT was studies with increasing number of bacteria. Data represent means=S.D. of two experiments each done in duplicate.

FIG. 26. A. In vivo effect of curliated *E.coli* on the clotting time. Three mice in each group were intravenously injected with YMel or YMel-1 bacteria in PBS. Blood was drawn one hour after infection and the aPTT of the resulting plasma samples were determined. Control samples were from the mice infected with PBS alone. B. Depletion of plasma fibrogen by curliated bacteria. Plasma samples generated as described above, were diluted ⅒, 1/20, 1/40 etc, in 0.15 M NaCl. Activated thrombin was added, and after 15 min the maximum dilution allowing fibrin polymerization was determined.

Figure 27:
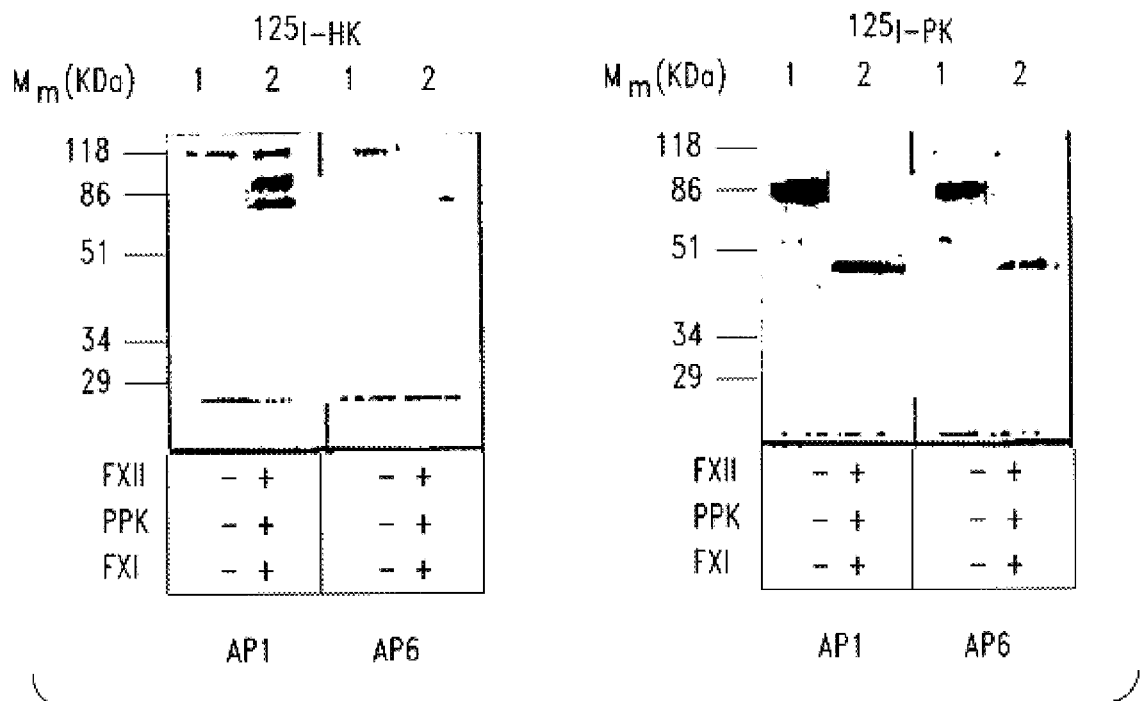

FIG. 27. Activation of contact phase system on the surface of AP1 and AP6. $^{125}$I-HK 25 µl of a solution containing radio-labeled HK ($4.6 \times 10^{-12}$ M) was incubated with 0.2 ml AP1 and AP6 ($2 \times 10^8$ cells/ml) in the absence or the presence of non-labeled F XII ($3.0 \times 10^{-12}$ M), PK ($3.9 \times 10^{-12}$ M), and F XI ($0.2 \times 10^{-12}$ M F XI) marked by plus or minus. After 10 min samples were centrifuged and run on SDS-PAGE under reducing conditions followed by autoradiography. $^{125}$I-PK Radio-labeled plasmakallikrein was incubated in the presence and the absence of non-labeled F XII, HK and F XI with AP1 and AP6 using the same concentrations as described above.

Figure 28:
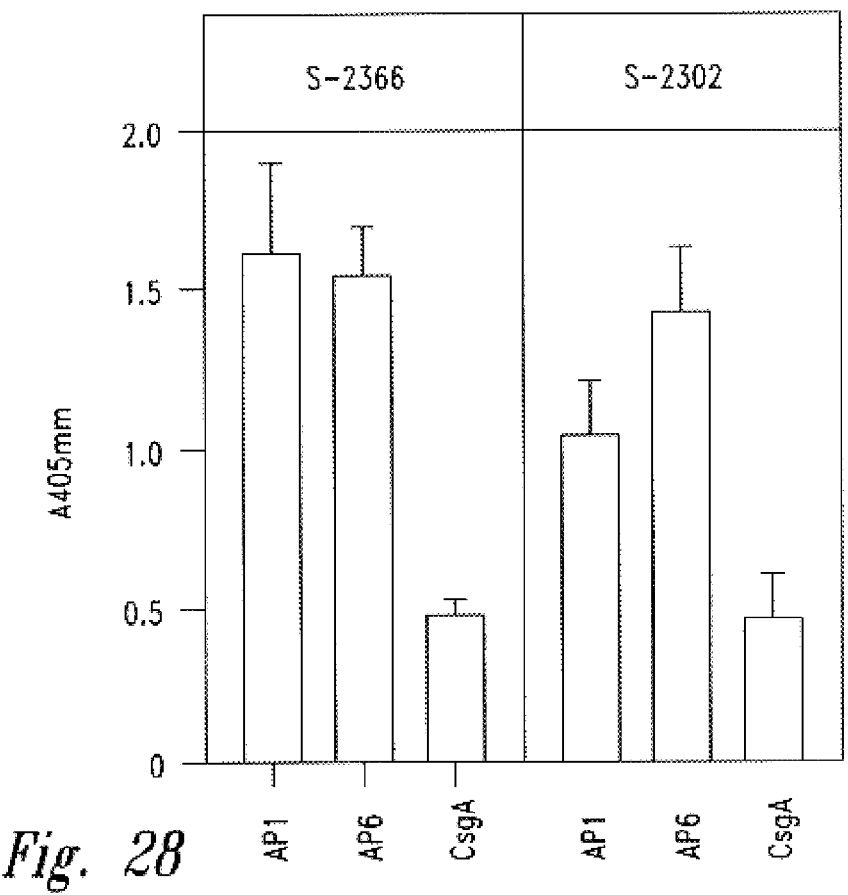

FIG. 28. Proteolytic activity on the surfaces of AP1 and AP6 after contact with plasma. 0.5 ml of human plasma was incubated with 0.5 ml of the strains AP1, AP6 and CsgA ($2 \times 10^{10}$ cells/ml) for 10 mins at room temperature. Bacteria were washed three times and amidolytic activities were tested by chromogenic substrate assays for F XI (S-2366) and for F XII/PK (S-2302). As a control, the strain CsgA was used, which fails to bind any of the contact phase factors.

FIG. 29. Effects of bacteria on the partial thromboplastin time (aPTT).

Panel A—30 µl of a bacterial solution of the strains AP1, AP6 and CsgA ($2 \times 10^{10}$ cells/ml) were incubated with 100 µl of sodium citrate treated plasma for 30 s. The clot formation was initiated by adding kaolin reagent and $CaCl_2$, and subsequently the partial thromboplastin time (aPTT, in seconds) was measured. As a control plasma incubated with only buffer was measured.

Panel B—Bacteria and plasma were pre-incubated as described above. But the clot formation was initiated in the absence of kaolin. As a control plasma incubated with only buffer was used.

Panel C—0.5 ml sodium citrate treated plasma were incubated with 0.5 ml of the strains AP1, AP6 and CsgA ($2 \times 10^{10}$ cells/ml) dissolved in the same buffer and incubated for 30 min at room temperature. After the bacteria were removed by centrifugation, 100 µl of the resulting solution were used to measure the aPTT. As a control, only buffer was added to plasma.

DETAILED DESCRIPTION OF THE INVENTION

We have demonstrated that the components of the contact phase system bind to the surface of some bacteria. In particular H kininogen is shown to bind to the surface of Streptococci and in particular to *S. pyogenes*. HK also binds to the surface of curli-expressing bacteria such as certain strains of *E. coli* and Salmonella. HK is also shown to release bradykinin when in contact with *Staphylococcus aureus*. Bradykinin is released from the bacterial bound HK in the presence of, for example, plasma killikrein.

Release of bradykinin from the bacterial surface stimulates an inflammatory response. Bradykinin is also a potent vasoactive peptide.

The other contact phase proteins are also shown to bind to the bacterial surface. The binding of prekallikrein and factor XI is mediated through the binding of HK. Factor XII also binds to the bacterial surface. Activated factor XII plays a role in the inflammatory cascade and coagulation cascade. In particular we have not found that the presence of bacteria which bind to the contact phase proteins and in particular which bind to F XII increases the clotting time of a plasma sample.

This has a further implications on the ways to treat severe bacterial infection and proposes the use of coagulation agents which enhance the ability of the plasma to form clots. Given that the bacteria appear to benefit from the binding of the contact phase components and use the inflammatory or coagulation cascades to assist in spread and virulence, the interactions between bacteria and the contact phase proteins can be used to assay for agents which interfere or modify these interactions. Monitoring the effect of HK and F XII binding to bacteria can also be used to identify new anti-inflammatory agents or coagulation agents which may be used in general to treat bleeding disorders and inflammation which are not necessarily caused by bacterial infection.

Candidate substances

A substance which interferes with activation of the contact phase system at the bacterial surface may do so in several ways. It may directly interfere with the binding of one or more of the contact phase components to the bacterial surface. Alternatively, it may interfere with the interaction of the contact phase components once bound on the bacterial surface or prevent activation of the contact phase system.

Candidate substances of each of these types may conveniently be screened by in vitro binding assays, for example, as described below. They may also be screened by in vitro assays for activation of the contact phase component, for example, by measuring release of kinin or by looking at the effect on coagulation times for example in a aPPT test, for example, as described below. Candidate substances may also be tested in vivo, for example, as described below.

Assays

The assays in accordance with the invention may be in vitro assays or in vivo assays, for example, using an animal model. In accordance with the invention, the bacterial strain to be used in the assay may be any bacteria which is shown to interact with the contact phase system. In particular, strains of Streptococci, preferably *S.pyogenes,* curli-expressing bacteria such as *E.coli* and Salmonella and other bacteria shown to bind any of the contact phase system components such as *Staphylococcus aureus* are suitable candidates for use in the assays of the invention.

The invention provides an assay having the following steps:
 a) including a plasma sample with a bacterial strain,
 b) adding the compound to be assayed
 c) conducting an aPTT test on the sample; and
 d) determining whether there is a decrease in the clotting time.

The invention has been described specifically with reference to an aPTT test Kits for such tests are commercially available. Other tests which would also demonstrate a decrease in the clotting time may be used in accordance with the invention. In particular, any test looking at coagulation in which the presence of bacteria are shown to effect the coagulation times would be a suitable test for use in accordance with the present invention.

Plasma may be obtained from a mammalian source such as human or mouse. The bacterial strain can be incubated with a sample of plasma which would contain all of the contact phase components. The assay may also be conducted in the absence of one or more of the usual contact phase components which would be present in plasma. Alternatively, the assay could be carried out in the presence of those plasma components which interact with the bacteria and are required for normal clotting times and any other components of the plasma alone which are necessary to conduct an aPTT test. Thus the assembly may be conducted by incubating bacteria solely in the presence of the plasma components required for clotting. For example, the components of the intrinsic pathway of coagulation may be incubated with the bacteria.

Assays according to the invention may be carried out in a number of different ways. In particular, the assay could be carried out both in the presence of a compound to be assayed and in the absence of the compound to be assayed. A comparison between the two assays could then be made to determine the effect of the compound to be assayed to determine whether that compound would be useful in the treatment of bacteria disorders. Alternatively, as a control, the assay could be carried out in the absence of any bacteria. Thus, in accordance with one aspect of the invention, the invention provides the steps of incubating a plasma sample with a bacterial strain
 adding a compound to be assayed to the sample
 conducting an aPTT test on the sample
 incubating a plasma sample with a bacterial strain and conducting an aPTT test on that sample
 determining whether there is a difference in the clotting time in the two samples.

In general, it would be expected that the bacterial strain would have the effect of increasing the clotting time, in particular the clotting time in an aPTT test. A compound which may be useful in the treatment of a bacterial induced coagulation disorder will have the effect of decreasing the clotting time when compared to the clotting time in the absence of the compound. The compound itself may additionally have an effect on the clotting time in the absence of bacteria and would still be useful in the treatment of bacterial induced coagulation disorders.

In an alternative aspect, the bacteria may be removed from the sample prior to carrying out the aPTT test. The bacteria may be removed from the sample prior to addition of the compound to be assayed. In part, this is due to the ability of bacteria to deplete the contact phase components from a sample. A compound which may be useful in the treatment of a bacterial induced coagulation disorder may have the effect of improving clotting times after such depletion of the contact phase components. Thus, in accordance with this aspect of the invention, the assay comprises the steps of incubating a plasma sample with a bacterial strain, removing bacteria from the sample, adding the compound to be assayed and conducting an aPTT test on the sample. These steps may also be carried out without including the step of adding the compound to be assayed. The clotting times of the two tests may be compared to assess the effect of the compound under assay.

The compound may be added to the sample before, during or after the bacterial, since the compound may at in any way to alter the clotting time. The assay can also be carried out as a challenge in an animal model with bacteria. Bacteria could be introduced into the animal to establish survival of the animals following bacterial infection. Candidate substance can be co-administered with the bacteria or subsequent to administration and prior to administration of bacteria to establish whether the candidate substance can improve survival. It is particularly preferred that animals will be challenged with bacteria. Blood samples can then be removed from the animal for use in the assays in accordance with the invention. Thus, in this embodiment, an animal is first challenged with a bacterial strain, a blood sample is taken from the animal,
 a compound to be assayed is added to the blood sample
 an aPTT test is carried out on the sample.
 the clotting time is determined.

This assay could also be carried out without adding the compound under assay so that a comparison could be made to determine the effect of the compound on the clotting time. It is also possible that the compound could be administered together with the bacteria so that a sample of blood is then taken from the animal and the aPTT test carried out on the blood sample. In an alternative assay method, binding of the contact phase proteins to the surface of bacteria can be determined. Any inhibitory effect by the candidate substance can then be evaluated. One type of in vitro assay for identifying substances which interfere with activation of the contact phase proteins on the bacterial surface involves incubating bacteria in the presence of one or more contact phase components in the absence of a contact substance; incubating bacteria with at least one contact phase component in the presence of a candidate substance; and determining if the candidate substance disrupts the interaction between bacteria and the contact phase component.

Alternatively, bacteria can be incubated with at least two or all of the contact phase components. Activation of the contact phase system following binding of the bacteria can be determined, for example, by measuring release of kinin from bound H-kininogen. As a control, the assay can be run in the absence of any bacteria. Similarly, any inhibitory effect by the candidate substance can be evaluated.

In this assay, the candidate substance can be incubated together with the bacteria and contact phase system. Alternatively, the bacteria may first be incubated together with the elements of the contact phase system. Subsequently, the candidate substance can be introduced.

When assaying for binding of contact phase components, labels may be used such as a radioactive label, an epitope tag or an enzyme antibody conjugated to the contact phase protein to determine the quantity of bound protein to the bacteria surface. The effect of a candidate substance on an interaction between bacteria and the contact phase components can be determined by comparing the amount of label bound in the presence of contact candidate substance with the amount of label bound in the absence of candidate substance. A lower amount of label bound in the presence of the candidate substance indicates that the candidate substance is an inhibitor of binding between the contact phase proteins and bacteria.

Therapeutic uses

A key part of the bacterial infection process which in particular may lead to toxic shock like syndrome and coagulation disorders involves activation of the contact phase system on the surface of bacteria. The present invention provides a substance capable of interfering with activation of the contact phase system or substances which inhibit the effects of activation of the contact phase system and provides the use of such substances in methods of treating bacterial infection.

The formulation of the substance according to the invention will depend upon the nature of the substance identified but typically a substance may be formulated for clinical use with a pharmaceutically acceptable carrier or diluent. For example, it may be formulated for topical, parenteral, intravenous, intramuscular, subcutaneous, intraocular or transdermal administration. A physician will be able to determine the required route of administration for any particular patient and condition.

Preferably, the substance is used in an injectable form. It may therefore be mixed with any vehicle which is pharmaceutically acceptable for an injectable formulation, preferably from a direct injection at the site to the treated. The pharmaceutically acceptable carrier or diluent may be, for example, sterile or isotonic solution.

The dose of substance used may be adjusted according to various parameters, especially according to the substance used, the age, weight and condition of the patient to be treated, to mode of administration used and the required clinical regimen. A physician will be able to determine the required route of administration and dosage for any particular patient and condition.

The invention will be described with reference to the following examples which are intended to be illustrative only and not limiting. It has been shown that kininogens bind to the surface of infectious bacteria such as *Streptococcus pyogenes, Escherichia coli* and Salmonella, and these results are presented in the appended examples 1 and 2. This binding causes activation of the so called contact phase system in which also prekallikrein, factor XI and factor XII participate. As a result proteolytic enzymes called killikreins are activated, and these enzymes are able to release kinins from kininogens. Kinins are short peptides of which bradykinin is the most important. These reactions are schematically outlined in FIG. 1.

Another microbial way of releasing kinins has also been found, and it is described in detail in example 3. *Streptococcus pyogenes* produces a cystein proteinase (se e.g. WO 96/08569) which directly can degrade H-kininogen thereby releasing physiologically active kinins. Thus Streptococcus pyogenes can induce release of kinis not only on the bacterial surface by activating the contact phase system, but also by producing SCP which is able to directly degrade H-kininogen in the blood stream.

As already mentioned bradykinin and other kinins are potential peptide hormonescausing fever, hypotension, increased vascular permeability, contraction of smooth muscles and pain. A massive release of kinis may therefore explain many of the symptoms observed during severe infection diseases.

By blocking the kinin effect with kinin antagonists these disease symptoms can be cured as is shown in tests on mice which are presented in example 4. These tests show that mice infected with lethal doses of *S. pyogenes* or of SCP live longer and look healthy and unaffected if they are treated with the bradykinin antagonist HOE 140 (Boa et al. (1991), Eur. J. Pharmacol., vol. 200, pp. 179–182).

The invention accordingly relates to use of kinin antagonists for preparing a pharmaceutical composition for treating and preventing bacterial infections. All pharmaceutically acceptable substances capable of preventing the physiological actions of kinins can be used according to the present invention. The kinin antagonists HOE 140 (Bao et al., supra), NPC 17751 (Mak et al. (1991), Eur. J. Pharmacol., vol. 194, pp. 37–43), NPC 349 (Wirth et al. (1995), Can. J. Pharmacol., vol. 73, pp. 797–804), CP0127 (Whalley et al. (1992), Agents, Actions Suppl., vol. 38(Pt3):pp. 413–20), NPC-1776 (Cheronis et al., eds.: Proteases, Protease Inhibitors and Protease-Derived Peptides (1993, Birkhauser Verlag, Basel, C11), pp. 167–176), WIN 64338 Sawutz et al (1995), Can. J. Physiol. Pharmacol., vol. 73, pp. 805–811), des-Arg9-[Leu81 bradykinin (Pruneau et al. (1996), Eur. J. Pharmacol, vol. 297 pp. 53–60), DesArg9-D Arg[Hyp3, Thi5,D-Tic7,Oic8]-bradykinin (desArg10-[HOE140]) (Wirth et al. (1991), Eur. J. Pharmacol., vol. 205, pp. 217–218) and Sar4-[D-Phe8]-des-Arg9-bradykinin (Gouin et al. (1996), vol. 28, pp. 337–43) and other suitable kinin antagonists disclosed in these articles are especially preferred. The antagonists can be used against infections caused by Gram positive and/or Gram negative bacteria. Ft is preferred to use them against infections caused by bacteria belonging to the genera Streptococcus., scherichia, Salmonella, Staphylococcus, Klebsiella, Moracella, Haemophilus and Yersinia.

Suitable pharmaceutical compositions comprises an effective amount of the kinin antagonist or a pharmaceutically acceptable derivative or salt thereof and one or more pharmaceutically acceptable inert carriers or excipients.

The compositions can be used for treating any warm blooded animal including humans.

The amount of the active compound may vary from 0.001% to about 75% by weight of the composition. Any pharmaceutically acceptable inert material which does not degrade or otherwise react with the antagonist can be used as a carrier.

The pharmaceutical compositions are prepared in a manner well-known to the skilled person. The carrier or excipient may be a solid, semisolid or liquid material which can serve as a vehicle or medium for the active ingredient.

The composition may be administered in any form or mode which makes the compound bioavailable in effective amounts, including oral and parenteral routes. It can, for example, be administered orally, subcutaneously, intramuscularly, intravenously, transdermally, intranasally, and rectally. Oral administration is preferred.

The active compound can be administered in the form of tablets, capsules, suppositories, solutions, suspensions etc.

The carrier may be an inert diluent or an edible carrier. The adjuvants may be binders such as microcrystalline cellulose, gum traganth, gelatine, starch or lactose; disintegrating agents such as alginic acid, primogel, corn starch; luricants such as magnesium stearate; glidants such as colloidal silicon dioxide, sweetening agents such as sucrose or saccharin or a flaving agent; liquid carriers such as polyethylene glycol or a fatty oil.

Tablets or pills may be coated with sugar, shellac or other enteric coatings.

Solutions or suspensions may also include sterile diluents such as water for injection, saline solution, fixed oils, polyethylene glycols, glycerine, propylene glycol or other synthetic solvents; chelating agents; buffers and agents for adjusting tonicity, such as sodium chloride or dextrose.

The invention will now be more closely described in the following examples.

EXAMPLE 1

M proteins are fibrous, hair-like structures expressed at the surface of Streptococcus pyogenes (Fischetti (1989), Clin. Microbiol. Rev, Vol 2, pp 285–314; Kehoe (1994), New Compr. Biochem., vol. 27, pp. 217–261). They are regarded as major virulence determinants due to their antiphagocytic property, and exist in more than 80 different serotypes. A role for M protein in fibrinolysis was suggested by the observation that some M proteins bind plasminogen (Berge et al. (1993), J. Biol. Chem. vol. 268, pp. 25417–25424).

S pyogenes is an important human pathogen causing common suppurative infections such as pharyngitis and skin infections, but also hyperacute and life-threatening toxic conditions as weft as serious post-infectious conditions (rheumatic fever and glomerulonephritis).

Bacterial strains and culture conditions.

S. pyogenes strains AP 1 (40/5 8) and AP46 (1/59), expressing the M 1 and M4 proteins, respectively, and the M negative strain AP74 (30/50) were from the Institute of Hygiene and Epidemiology, Prague, Czech Republic. Bacteria were grown in Todd Hewitt, broth (Difco) at 37° C. for 16 hours, washed twice in PB S (0. 15 M NaCl, 0. 02 M phosphate, pH 7.4) containing 0.02% $NaN_3$ (w/v) (PBSA), and resuspended in PBSA to $2 \times 10^{10}$ cells/ml. Cells from this stock suspension were used in plasma absorption experiments and kallikrein digestions assays.

Proteins and labeling of proteins

Kininogens were purified from human plasma as previously described (Muller Esterl et al. (1988), Methods Enzymol., vol. 163, pp. 240–256). The monoclonal antibody HKL 16 directed to an epitope in domain 6 (domain D6H) of the light chain of HK was raised in mouse and affinity purified on protein A-Sepharose (Kaufmann et al.(1993), J. Biol. Chem. vol. 268, pp. 9079–9091). The monoclonal antibody HKL 19, also directed against the D6H domain of HK, has been described (Kaufmann et al.(1993), J. Biol. Chem., vol. 268, pp. 9079 9091). Prekallikrein was isolated from human plasma (Hock et al. (1990), J. Biol. Chem. vol.265, pp. 12005–12011). Human factor XI was a kind gift of Dr. J. Meijers, Department of Hermatology, University of Utrecht, The Netherlands. Human factor XII was from Enzyme Research Laboratories, South Bend, Ind., USA Recombinant M1 and M46 proteins were produced as described (Berge et al., supra; Akesson et al. (1994), Biochem. J. vol. 877–886).

Plasma absorption Experiments

The plasma absorption experiments were performed as described (Sjobring et al.(1994), Mol. microbiol. vol. 14,pp. 443–452). Fresh human plasma was mixed with proteinase inhibitors (Sigma Chemical) to a final concentration of 2 mM aprotinin, 0.1 mM diisopropylfluorophosphate (DFP), 1 mM soy bean trypsin inhibitors (SBTI), 0.1 mM phenylmethylsulfonylfluoride (PMSF), and 5 mM benzamidine chloride. Bacteria ($2 \times 10^{10}$ cells/ml) suspended in 1 ml PBST (PBS containing 0.05% Tween 20) were incubated with 1 ml human plasma for 60 min at 37° C. The cells were pelleted and washed three times with 10 ml of PBST. To elute the absorbed proteins, the bacteria were incubated for 5 min with 0.5 ml of 30 mM HCl, pH 2.0. The bacteria were pelleted and the supernatant was immediately buffered with 50 μl of 1M Tris, concentrated to 250 μl (with a buffer change to PBS) by ultrafiltration on an Amicon Centricon-30 (Amicon Inc. Beverly, Mass. U.S.A.). Twenty microliters of the protein solution was analysed by SDS-PAGE and immunoprint experiments using the monoclonal antibody HKL16.

ELISA

The Sandwich ELISA technique was performed as detailed (Muller-Esterl et al. (1988), supra; Kaufmann et al. (1993), supra; Kaufmann (1993), Annu. Rev. Immunol. vol. 11, pp. 129–163) with modifications as follows; microtiter plates (Immunolon, Dynatech) were coated with 1 μg/ml of the monoclonal antibody HKL19 in 15 mM $NaHCO_3$/$Na_2CO_3$ buffer, pH 9.6, containing 1.5 mM $NaN_3$ by overnight incubation at 4° C. The plates were washed five times with 20 mM phosphate buffer, pH 7.4, containing 150 mM NaCl and 0.05% (w/v) Tween 20 (PBST). Serial doubling dilutions of HK standards (starting at a concentration of 2 μg/ml) or samples were prepared in PBST containing 2% BSA and 200 μl were added to the coated wells in duplicate. After incubation for 1 hour at 37° C. and washing as above, 200 μl of a polyclonal anti-HK sheep IgG diluted 1:1000 in PB ST containing 2% BSA were applied per well followed by incubation for 2 hours at 37° C. The plates were extensively washed (see above) and 200 μl of a POD-conjugated antisheep secondary antibody was added and incubated for 2 hours at 37° C. Finally, after washing as above, 200 μl of 0.1% (w/v) ABTS (2,2'azino-bis(3-ethyl2,3-dihydrobenzthiazoline)-6-sulfonate), 0.05% (v/v) $H_2O_2$ in 0.1 citric acid, 0.1 M NaHPO, were added to each well and the plates were incubated for 30 min at 37° C. in the dark. The change in absorbance at 405 nm was measured, and the amounts of HK in the samples determined using the HK standard curve.

Electrophoresis and electroblotting

SDS-PAGE (polyacrylamide gel electrophoresis) was performed as described (Neville (1971), J. Biol. Chem., vol. 246, pp. 6328–6334). Proteins in eluates from absorption experiments with bacteria were separated on gels of 10% total acrylamide with 3% Bisacrylamide. Before loading, samples were boiled for 3 min in sample buffer containing 2% SDS and 5% β-mercaptoethanol. For Western blotting analysis, proteins were transferred to polyvinylidenedifluoride (PVDF) membranes (Immobilon, Millipore) by electroblotting from gels as described (Towbin et al. (1979), PNAS, vol 76, pp. 4350–4354) using a Trans Blot semi-dry transfer cell (Bio-Rad, Irvine, Calif., U.S.A.).

Determination of affinity constants

Binding kinetics were determined by surface plasmon resonance spectroscopy using a BIAlite biosensor system (Pharmacia Biosensor AB, Freiburg, Germany). HK was immobilised on research grade CM5 sensor chips in 10 mM sodium acetate, pH 4.5, using the amine coupling kit supplied by the manufacturer. All measurements were carried out in HEPES-buffered saline that contained 10 mM HEPES, pH 7.4, 150 mM NaCl, 3.3 mMEDTA, and 0.005% Surfactant P.20 (Pharmacia Biosensor AB). Analyses were performed at 25° C. and at a flow rate of 10 μl/min. to calculate affinity constants, 30 μl of streptococcal M1 protein and M46 protein were applied in a serial dilution (starting concentration 100 μg/ml) followed by injection of buffer alone (30 μl). In addition, 30 μl of plasmakallikrein samples (doubling dilution; starting concentration of 25 μg/ml) were assayed for comparison. Surfaces were regenerated with 30 μl of 10 mM HCl at a flow rate of 10 μl/min. The kinetic data were analysed by the BIA evaluation 2.0 program (Pharmacia Biosensor AB). Alternatively, 30 μl of M1 protein (50 μg/ml) and plasmakallikrein (10 μg/ml) alone or in combination were added and the amount of bound protein was determined, expressed in resonance units (RU) according to the manufacturer's descriptions.

Immunoprint analysis of HK and its fragments

Immunoprint analysis was performed as follows. Briefly, the PVDF membranes were blocked in PBST containing 5% (w/v) nonfat dry milk for 20 min at 37° C. (Timmons et al. (1990), Methods Enzymol. vol. 182, pp. 679–688), washed three times with PBST for 5 min and incubated with antibodies against HK (in the blocking buffer) for 30 min at 37° C. After washing the sheets were incubated with peroxidase-conjugated secondary antibodies for 30 min at 37° C. Secondary antibodies were detected by the chemiluminescence method (Timmons et al. (1990), supra; Nesbitt et al. (1992), Anal. Biochem., vol. 206, pp. 267–272). Autoradiography was done at room temperature for 1–2 min using Kodak X-Omat S films and Cronex Extra Plus intensifying screens.

Kallikrein digestion assay and quantification of released bradykinin

Plasma prekallikrein was activated to plasma kallikrein by cleavage with activated factor XIIa as described (Berger et al. (1986), J. Biol. Chem., vol. 261, pp. 324–327). Briefly, plasma prekallikrein was mixed with factor XIIa in a molar ratio of 10:1 in PBS, pH 7.4, and incubated for 2 hours at 37° C. and immediately used for proteolysis experiments (see below). Bacteria ($4 \times 10^{10}$ cells) in 0.5 ml PBST were incubated with 1.5 ml human plasma diluted 2:1 in PBST containing protease inhibitors (see Absorption experiments). After incubation for 1 hour at 37° C. the cells were washed three times in 10 ml PBST and resuspended in 0.4 ml kallikrein assay buffer, 0.15 m Tris-HCl, pH 8.3 (Hock et al. (1990), supra). Bacteria were mixed with 100 μl of plasma kallikrein (giving a final enzyme concentration of 0.02 μg/ml) in an Eppendorf tube and incubated for 10 min at 37° C. An equal amount of bacteria suspension was incubated, as a control, with 10 μg kallikrein assay buffer without kallikrein. The incubation was ended by adding 0.4 ml of 60 mM HCl. Cells were pelleted and the supernatants were immediately buffered by adding 100 μl of 1 M Tris and ultrafiltrated through an Amicon Centricon-10 filter (Amicon Inc.) to separate free BK from kininogen fragments. The resulting filtrates were analysed for their BK content by solid phase radioimmunoassay using the MARKIT-M bradykinin TM kit (Dainippon Pharmaceutical Co., Osaka, Japan).

Results

HK is absorbed from human plasma by M protein-expressing *S. pyogenes* bacteria

M proteins are known to interact with a number of different plasma proteins including fibrinogen, plasminogen, immunoglobulins, albumin, and factor H and C4 binding protein of the complement system (Kehoe (1994), supra). This raises the question whether the interaction between HK and M protein can take place in the presence of these other M protein binding plasma proteins, especially as proteins like albumin, IgG, and fibrinogen occur at much higher concentrations than HK (HK represents approximately 0.15% of the total protein content in plasma). To address this question two strains of *S. pyogenes* expressing M1 and M46 protein, respectively, were incubated with fresh human plasma. Following extensive washing, proteins bound to the bacterial surface were eluted and the amount of HK was determined by ELISA. In a representative experiment the amounts of HK eluted from M1 and M46 bacteria were 63.6 and 123.6 pmol/$10^{13}$ bacteria, respectively, whereas an M protein negative mutant strain (AP74) absorbed HK at background level (below 10 pmol/$10^{12}$ bacteria). The results demonstrate that HK also in a plasma environment can interact with M protein-expressing *S. pyogenes* bacteria.

Figure 4A:
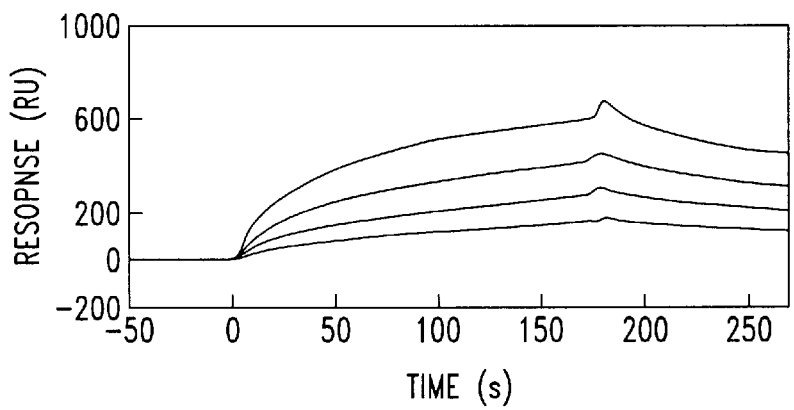
FIG. 4 shows analysis of the interactions between H-kininogen and MI protein, and H kininogen and plasma prekallikrein. This is illustrated by an overlay plot of the binding of M 1 protein (A) and plasma prekallikrein (B) to immobilized HK using plasmon resonance spectroscopy. Increasing concentrations of MI protein (12.5, 25, 50, and 100 μg/ml) or plasma prekallikrein (3.13, 6.25, 12.5 and 25 μg/ml) were applied for 3 min each during the association phase. Dissociation of bound proteins was measured following injection of buffer alone.
Figure 4B:
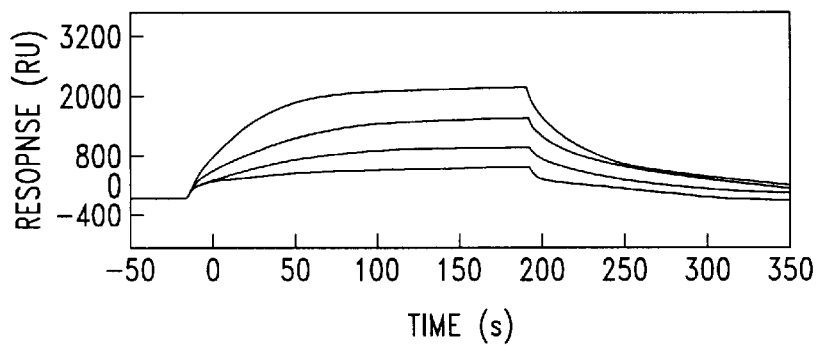

Analysis of the binding of M proteins to HK suggests that HK is accumulated at the streptococcal surface Using surface plasmon resonance spectroscopy, the binding kinetics between HK and the M1 and M46 proteins were determined and compared to the interaction between HK and plasma prekallikrein. In these experiments different amounts of purified M proteins or plasma prekallilrein were applied and left to interact with immobilised HK to the level of saturation. FIG. 4 shows typical sensorgrams obtained between HK and M1 protein (4A) and plasma prekallikrein (4B). The results obtained for HK-M46 (not shown) were similar to those for HK-M1 shown in FIG. 4A. On the basis of these experiments, dissociation and association rates were calculated, which when divided give the dissociation constants (Table 1). The figures demonstrate that the dissociation of M1 and M46 proteins are slower than their association, permitting an accumulation of HK at the bacterial surface. It can also be noted that the HK affinity is higher for M46 than for M1 protein. In plasma, prekallikrein circulates in complex with HK. As shown in FIG. 4B and Table 1, both the association and dissociation rates are high for the interaction between these proteins. However, different data suggest that the binding of M proteins to HK is not disturbed by the interaction between plasma prekallikrein and HK. Thus, prekallikrein interacts with HK through the D6H domain, residues 569–595 (Berger et al. (1986), supra), whereas the binding site for M1 protein in HK is in domain D5H, residues 479–496 (Ben Nasr et al. (1996), Mol. Microbiol. vol. 14, pp. 927–935). Moreover, when a sample containing both M1 protein and prekallikrein was applied to an HK-coupled sensor chip, a binding of 909 RU was recorded (FIG. 4A) which represents almost 100% of the calculated maximum binding. In other experiments the binding of plasma prekallikrein to preformed complexes between HK and M1 protein was studied (FIG. 4B). The results of these experiments also suggest that M1 protein and plasma prekallikrein can bind simultaneously to HK. Finally, this is also supported by the fact that plasma prekallikrein in an indirect ELISA (Berger et al. (1986), supra) was absorbed by HK bound to immobilised M1 protein (data not shown).

HK is cleaved at the surface of *S. pyogenes*

Figure 5:
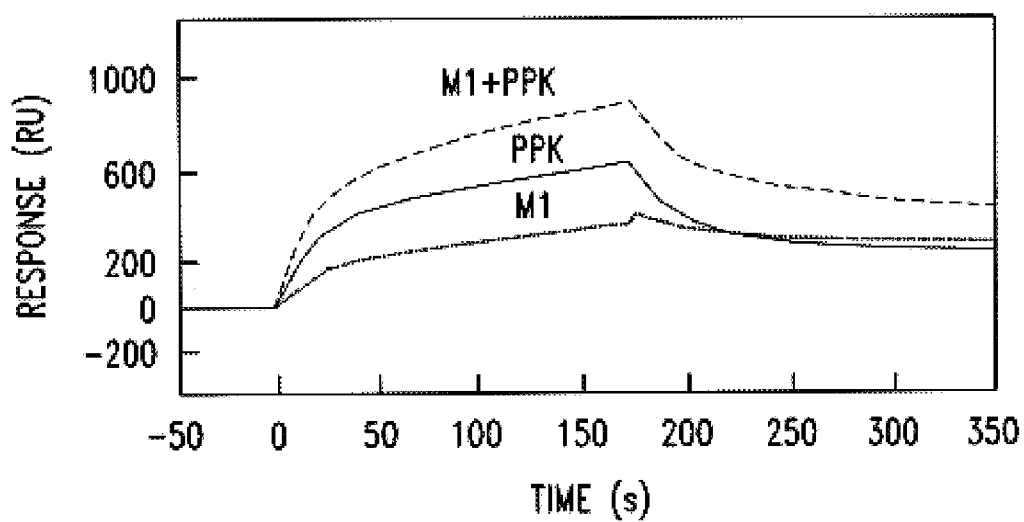
FIG. 5, which is of the same type as FIG. 4, shows that M 1 protein and plasma prekallikrein do not compete for the same binding-site in H-kininogen. M1 protein (30 μl, 50 μg/ml) and plasma prekallikiein (30 μl, 10 μg/ml) were applied to a sensor chip coupled with HK. Furthermore, a 30 μl sample containing both proteins (50 μg/ml M protein and 10 μg/ml plasma prekallikrein) were assayed. Samples were also applied as above except that plasma kallikrein was added following complex formation between M1 protein and HK.
Figure 6:
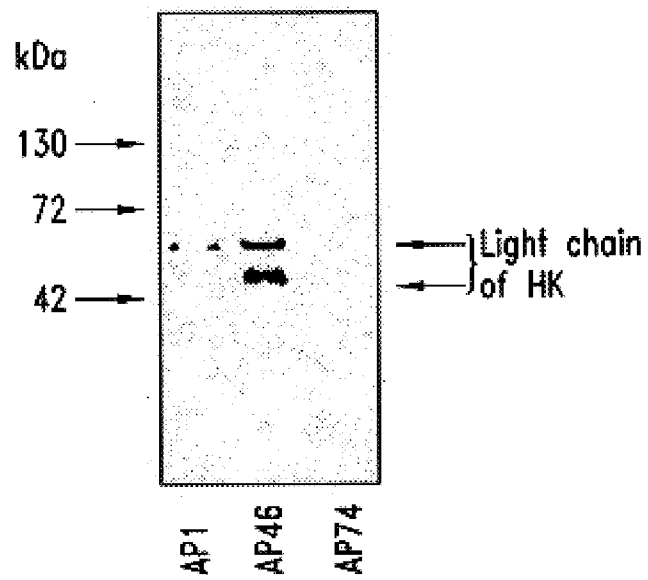
FIG. 6 discloses a Western blot analysis revealing that H-kininogen bound to the streptococcal surface is cleaved. Following incubation with human plasma, bacteria of strains AP 1, AP46, and the M protein-negative mutant strain AP74 were treated with glycine buffer, pH 2.0, to solubilize plasma proteins bound to the bacteria. The resulting supernatants were subjected to SDS-PAGE (10%) under reducing conditions. One gel with the sample was run. It was electroblotted to a PVDF membrane. The membrane was probed with monoclonal antibodies against the light COOH-terminal chain of HK, followed by peroxidase-labeled secondary antibodies (BLOT).
Figure 7:
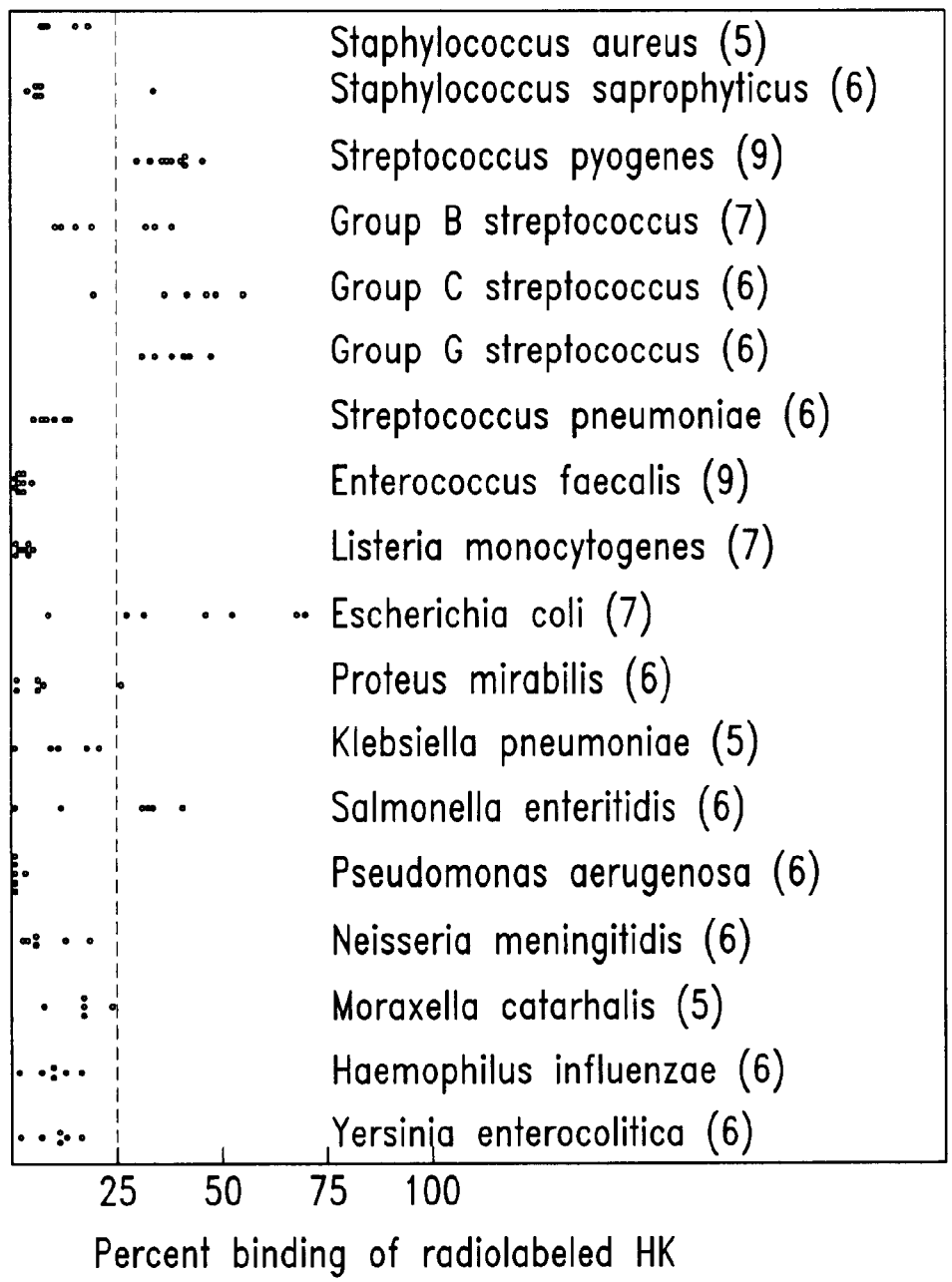
FIG. 7 relates to binding of radiolabeled H-kininogen to various bacterial species. In total 118 strains, all isolated from patients with sepsis, belonging to 18 different bacterial species were tested for binding of $[^{125}I]$-HK. Each dot represents one strain and figures within parenthesis indicate the number of tested strains of a given species.

Using antibodies against the light chain of HK in Western blot experiments, we analyzed the HK bound to and eluted from M protein-expressing bacteria. Intact HK has a molecular mass of 121 kDa and the release of the BK nonapeptide from HK results in the formation a two-chain molecule with a heavy and a light chain (63 and 58 kDa, respectively) connected by a disulfide bond. The light chain is in the COOH-terminal part of HK and as shown in FIG. 5 the antibodies against this chain bind to two bands corresponding to the light chain of 58 kDa, and a 45 kDa fragment of the light chain. No band is seen at the place for HK (121 kDa), demonstrating an efficient cleavage of HK at the bacterial surface. These results 18 suggest that HK is released as a consequence of the binding of HK to the streptococci, as HK in plasma occurs only in its intact form (Silverberg et al. (1988), Methods Enzymol., vol. 163, pp. 85–95). Moreover, HK in plasma incubated with the M-protein-negative *S. pyogenes* strain AP74 (Ben Nasr et al. (1995), Biochem. J, vol. 305, pp. 173–180) showed no degradation, a result which was not affected by the presence or absence of proteinase inhibitors in the plasma sample. The step-wise proteolysis of HK leading to BK release starts with the generation of a heavy chain in which the bradykinin peptide is still attached at the COOH-terminal end. Secondary cleavage by activated plasma prekallikrein then releases the BK peptide. When activated plasma prekallikrein was added in excess to the plasma proteins bound to the streptococci, BK was released and quantified. The level of BK release from strains AP1 and AP46 were 10.7±2.7 and 19.8±7.9 pmol/$10^{12}$ bacteria, respectively (values are the means of three experiments=1 standard deviation). However, in parallel experiments where activated prekallikrein was added to AP74 bacteria preincubated with human plasma, no release of BK was detected.

TABLE 1

Affinity rates and dissociation constants for the interactions between immobilised HK and M1 protein, M46 protein, or plasma prekallikrein*

|  | association rate ($10^3 \times s^{-1} M^{-1}$) | dissociation rate ($10^{-3} \times s^{-1}$) | dissociation constant ligand ($10^{-4} \times M$) |
| --- | --- | --- | --- |
| MI protein | 5.5 ± 0.8 | 3.7 ± 0.7 | 68.3 ± 15.7 |
| M46 protein | 9.5 ± 2.1 | 2.3 ± 0.3 | 24.8 ± 5.9 |
| Prekallikrein | 496 ± 128 | 18.3 ± 5.4 | 3.8 ± 1.3 |

*Values are mean ± SEM from at least three different experiments.

Example 2

Assembly of human contact phase proteins and release of bradykinin at the surface of curli-expressing *Escherichia coli*

In the present invention, a number of bacterial strains, belonging to several species and isolated from patients with sepsis, are tested as concern their different abilities to bind HK. In addition, the interaction between factors of the contact phase system and *E. coli* is analysed.

Bacterial strains and culture conditions 108 bacterial strains of human sepsis origin were isolated at the Department of medical Microbiology, Lund University, Lund, Sweden. Six *Streptococcus pyogenes* strains from patients with sepsis, isolated in Sweden between 1980–89, were kindly provided by Dr. Stig Holm Umea University, Umea, Sweden. Seventeen *E. coli* strains causing different gastrointestinal infections were kindly provided by Dr. James P. Nataro, from the Center for Vaccine Development University of Maryland School of Medicine, Baltimore, Md. The strains are designated EHEC 1-4 (84-7025; 83-8006; 78-534; 84-7453); EIEC 1-4 (IC651-1; 1C711-1; EI705-1; EI439-1). EPEC 1-4 (147-150983; 2348/69; 2087-77; 2395-80), ETEC 1-5 (EI142-4; E17-10; EI123-3; EI166-9; EI150-9) YMel is a curli-expressing *E. coli* K12 strain (Richenberg, H. V., and Lester, G. (1955) The preferential synthesis of beta-galactosidase in *Escherichia coli*. *J Gen Microbiol* 13: 279–284,1955). YMel-1 is an isogenic curli-deficient mutant strain generated by insertional mutagenesis of the csgA gene in YMel (Olsen, A, Arnqvist, A., Hammar, M., Sukupolvi S., and Normark, S. (1993) The RpoS sigma factor relieves H-NS-mediated transcriptional repression of csgA, the subunit gene of fibronectin binding curli in *Escherichia coli, Mol Microbiol* 7: 523–536). All Gram-positive species and the *Moraxella catarrhalis* strains were grown in Todd-Hewitt broth (Difco) at 37° C. for 16 hours. *Haemophilius influenzae, Neisseria meningitidis* were grown on brain-heart infusion supplemented with Haemin and nicotinamid. All other Gram-negative species were grown on Luria-Bertani (LB) broth for 16 h at 37° C. In some experiments, *Salmonella enteritidis* and *E. coli* species, designated ES 1-7 (for *E. coil* sepsis isolate number 1-7), were grown on LB- or colonisation factor agent (CFA)-agar (Evans, D. G., Evans, J. D. J., and Tjoa, W. (1977) Hemagglutination of human group A erythrocytes by enterotoxigenic *Escherichia coli* isolated from adults with diarrhoea: correlation with colonization factor, *Infect Immun* 18: 330–337) at 26° C. for approximately 40 h at 26 or 37° C. Bacteria were washed twice in PBS (0.15 M NaCl 0.06 M phosphate, pH 7.2) containing 0.02% $NaN_3$ (w/v) (PBSA), and resuspended in PBSA to $2 \times 10^{10}$ cells/ml Cells from this stock suspension were used in protein binding assays or in plasma absorption experiments.

Proteins and labeling of proteins

Kininogens were purified from human plasma as previously described (Muller-Esterl W., Johnson, D A, Salvesen, G., and Barrett, A. J. (1988) Human kininogens. *Methods Enzymol* 163: 240–256). The monoclonal antibody HKL16 directed to an epitope in domain 6 (domain D6H) of the light chain of HK was raised in mouse and affinity purified on protein A-Sepharose (Kaufmann, L, Haasemann, M., Modrow, S., and Muller-Esterl, W. (1993) Structural dissection of the multidomain kininogens. Fine mapping of the target epitopes of antibodies interfering with their functional properties. *J Biol Chem* 268: 9079–9091). The polyclonal anti-bradykinin antibodies, α-BK (AS348) were raised in rabbit using a conjugate of bradykinin and keyhole limpet hemocyanin covalently coupled by the carbodiimide method. Prekallikrein was isolated from human plasma (Hock, L, Vogel, R., Linke, R-P., and Muller Esterl, W. (1990) High molecular weight kininogen-binding site of prekallikrein probed by monoclonal antibodies. *J Biol Chem* 265: 12005-12011). Human factor XI was a kind of Dr. J. Meijers, Department of Hematology, University of Utrecht The Netherlands. Human factor XII was from Enzyme Research Laboratories, South Bend, Ind., U.S.A. Bovine serum albumin (BSA), human serum albumin (HSA), fibrinogen, fibronectin, and plasminogen were from Sigma Chemical (St. Louis, Mo.). Purification of curli from the *E coli* strain YMel was performed as described (Collinson, S. K., Emody, L., Muller, K.-H., Trust, T. L, and Kay, W. W (1991) Purification and characterization of thin, aggregative fimbriae from *Salmonella enteritidis*. *JBacteriol* 173: 4773–4781; Olsen, A. X., Hanski E., Normark, S., and Caparon, M. G. (1993) Molecular characterization of fibronectin binding proteins in bacteria. In *J Microbiol. Methods*. Boyle, M. D. P. (ed). London: Elsevier Science Publisher, pp. 213–226). The M1 protein and the PCR-generated M1 protein fragment (S-C3) were produced as described (Akesson, P, Schmidt, K.-H., Cooney, L, and Bjorch L. (1994) M1 protein and protein H: IgGFc- and albumin-binding streptococcal surface proteins encoded by adjacent genes. *Biochem J*300: 877–886). Proteins were labeled with $I^{125}$ using the Bolton and Hunter reagent (Amersham Corp., U.K.).

Bacterial binding assay

Bacteria were resuspended in PBSA containing 0.05% (w/v) of Tween-20 (PBSAT) and the cell concentration was adjusted to $2\times10^{10}$ cells per ml. Bacteria were diluted as indicated, and 200 µl of the resulting suspensions was incubated with radiolabeled protein in 25 µl PBSAT ($10^4$ cpm) at 37° C. for 60 min. For screening of the different bacterial isolates, dilutions of $2\times10^9$ cells/ml were used. After incubation two ml of PBSAT was added, the cell suspension was centrifuged, and the radioactivity of the pellet was counted. The binding activity was expressed as the percentage of the total radioactivity added per tube.

Absorption experiments

The plasma absorption experiments were performed as described (Sjobring, U., Pohl, G., and Olsen, A. (1994) Plasminogen, absorbed by *Escherichia coli* expressing curli or by *Salmonella enteritidis* expressing thin aggregative fimbriae, can be activated by simultaneously captured tissue-type plasminogen activator (t-PA), *Mol Microbiol* 14: 443–452) with some modifications. Fresh human plasma was mixed with protease inhibitors (Sigma Chemical) to a final concentration of 2 mM aprotinin, 0.1 mM diisopropylfluorophosphate (DFP), 1 mM soy beam trypsin inhibitors (SBTI), 0.1 mM phenylmethylsulfonylfluoride (PMSF) and 5 mM benzamidine chloride. Bacteria ($2\times10^{10}$ cells/ml) suspended in 1 ml PBST (PBS containing 0.05% Tween 20) were incubated with 1 ml human plasma for 60 min at 37° C. The cells were pelleted and washed three times with 10 ml of PBST. To elute the absorbed proteins, the bacteria were incubated for 5 min with 0.5 ml of 30 mM HCl, pH 2.0. The bacteria were pelleted and the supernatants was immediately buffered with 50 µl of 1M Tris, concentrated to 250 µl (with a buffer change to PBS) by ultrafiltration on an Amicon Centricon-30 (Amicon Inc. Beverly, Mass., U.S.A.). Ten microliters of the protein solution was analysed by SDS-PAGE and immunoprint experiments using antibodies to HK or bradykinin.

Electrophoresis and electroblotting

SDS-PAGE was performed as described (Neville, D. M. J. (1971) Molecular weight determination of protein-dodecyl sulphate complexes by gel electrophoreses in a discontinuous buffer system. *J Biol Chem* 246: 6328–6334). Plasma proteins and the proteins in eluates from absorption experiments with bacteria were separated on gels of 10% total acrylamide with 3% Bis-acrylamide. Before loading, samples were boiled for 3 min in sample buffer containing 2% SDS and 5% mercaptoethanol. Curli-subunits were separated on gels of 13.6% total acrylamide. Curli-containing preparations were not boiled prior to electrophoresis. For Western blotting analysis, proteins were transferred to polyvinylidenedifluoride (PVDF) membranes (Immobilon, Millipore) by electroblotting from gels as described (Towbin, R., Staehelin, T., and Gordon, J. (1979) Electrophoretic transfer of proteins from polyacrylamide gels to nitrocellulose sheets: Procedure and some applications. *Proc Natl Acad Sci USA* 76: 4350–4354) using a Trans Blot semi-dry transfer cell (BioRad, Irvine, Calif., U.S.A.). The membranes were blocked and washed at 37° C., and incubated with [$^{125}$I]-labeled proteins as described (Sjobring et al., 1994, op. cit). Autoradiography was done at –70° C. using Kodak X-Omat S films and Cronex Xtra Plus intensifying screens.

Immunoprint analysis of HK and its fragments

For immunoprint analysis of the electrotransferred proteins following plasma absorption experiments, the PVDF membranes were blocked in PBST containing 5% (w/v) nonfat dry milk for 20 min at 37° C. (Timmons, T. M., and Dunbar, S. D. (1990) Protein blotting and immunodetection. *Methods Enzymol* 182: 679–688), washed three times with PBST for 5 min and incubated with antibodies against HK (from mouse or rabbit, 2 µg/ml in the blocking buffer) for 30 min at 37° C. After washing the sheets were incubated with peroxidase-conjugated secondary antibodies against mouse or rabbit IgG (rabbit anti-mouse and sheep anti-rabbit, respectively) for 30 min at 37° C. Secondary antibodies were detected by the chemiluminescence method (Nesbitt, S. A., and Horton, M. A. (1992) A non-radioactive biochemical characterization of membrane proteins using enhanced chemiluminescence. *Anal Biochem* 206: 267–272). Autoradiography was done at room temperature for 1–2 min using Kodak X-Omat S films and Cronex Extra Plus intensifying screens.

Competitive binding, assay and affinity constant determination

Constant amounts of purified, polymeric curli (Olsen et al., 1993, op.cit) and [$^{125}$I-HK were incubated with varying amount of unlabeled HK. All reagents were diluted in incubation buffer (PBST containing 0.25% (w/v) BSA) to a total volume of 250 µl, incubated for 3 hours at 37° C. under gentle shaking, washed with incubation buller, and centrifuged for 15 min at 3000 g. The radioactivity of the resulting pellet was measured and the affinity constant was calculated as described (Akerstrom, B., and Bjorck, L. (1989) Protein L: an immunoglobulin light chain-binding bacterial protein. Characterization of binding and physicochemical properties. *J Biol Chem* 264: 19740–19746) using the formula of Scatchard (Scatchard, G. (1949) The attractions of proteins for small molecules and ions, *Ann N Y Acad Sci* 51: 660–672).

Kallikrein digestion assay

Plasma prekallikrein was activated to plasma kallikrein by cleavage with activated factor XIIa as described (Berger, D., Schleuning, W. D., and Schapira, M. (1986) Human plasma kallikrein. Immunoaffinity purification and activation to α- and β-kallikrein. *J Biol Chem* 261: 324–327). Briefly, plasma prekallikrein was mixed with factor XIIa in a molar ratio of 10:1 in PBS, pH 7.4, and incubated for 2 hours at 37° C. and immediately used for proteolysis experiments (see below). Bacteria ($5\times10^{10}$ in 0.5 ml PBST were incubated with 1.5 ml human plasma containing protease inhibitors (see "Absorption experiments"). After incubation for 1 hour at 37° the cells were washed three times in 10 ml PBST and resuspended in 0.5 ml kallikrein assay buffer, 0.15 m Tris-HCl, pH 8.3 (Hock et al, 1990, op. cit). Aliquots of 100 µl bacterial suspension in Eppendorf tubes were incubated with plasma kallikrein for 5, 10, 20 and 40 min at 37° C. One sample was incubated in the absence of kallikrein for 40 min at 37° C. At indicated times, 0.5 ml of 100 mM HCl was added to the mixtures, and the samples were incubated for 5 min at room temperature to allow the absorbed proteins to dissociate. The cells were pelleted and the supernatant was immediately buffered by adding 50 µl of 1 M Tris. The supernatants, were concentrated to 50 µl (with a buffer change to PBS) by ultra filtration on an Amicon Centricon-30 (Amicon Inc.). Twenty µl of the protein solution was analysed by SDS-PAGE followed by Western blotting and immunostaining using the polyclonal anti-bradykinin antibodies (α-BK).

Results

Several pathogenic bacterial species bind kininogens

It has previously been demonstrated that most strains of the human pathogen *Streptococcus pyogenes* bind kininogens through M proteins, a fibrous surface protein and virulence determinant. According to the present invention, it has now been shown that strains of several other pathogenic bacterial species, both Gram-positive and Gram-negative, isolated from patients with sepsis, also bind kininogens, especially H-kininogen (HK).

Figure 8:
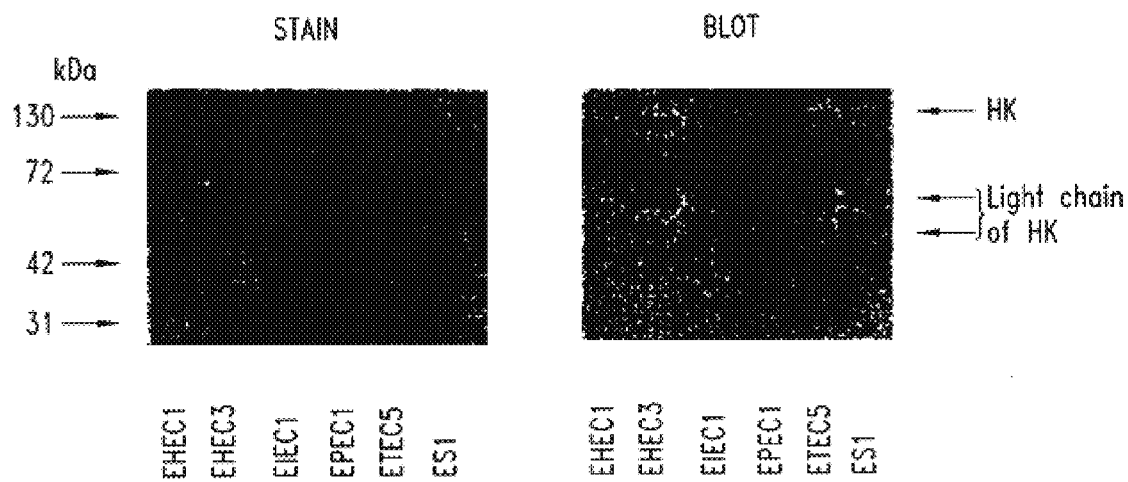
FIG. 8 relates to absorption of H-kininogen from human plasma by different strains of E. coli. Bacteria were incubated with human plasma for 60 min at 37° C. Following extensive washing proteins bound to the bacteria were eluted at pH 2.0. The eluted proteins were subjected to SDS-PAGE (10%) run under reducing conditions and stained with Coomassie Blue (STAIN). A replica of the gel was electrotransferred to a PVDF membrane which was probed with monoclonal antibody HKL 16 followed by secondary peroxidase-labeled antibody (BLOT).

A total of 118 bacterial strains, all isolated from patients with sepsis and belonging to 18 different species, were tested for binding of radiolabeled HK and LK at pH 7.2 in PBS. HK and LK share their NH$_2$-terminal domains D1–D4, whereas they differ in their COOH-terminal domains (see Miffier-Esterl et al., 1988). The majority of β-haemolytic streptococcal strains and E. coli and Salmonella enteritidis strains bound more than 25 percent of added M whereas many strains of Staphylococcus aureus, Streptococcus pneumoniae, Klebsiella pneumoniae, Moraxella catarrhalis, Haemophilus influenzae, and Yersinia enterocolitica bound 10–25 percent. Strains of the remaining species were mostly negative (binding below 10 percent). All the strains were also tested for binding of LK. Apart from some of the E. coli isolates which bound up to 40 percent the other strains showed low or background interaction. It was observed that culture conditions affected the binding of HK to E. coli and S. enteritidis. Thus, binding activities were clearly higher when the strains were tested following growth at 26° C., as compared to bacteria grown at 37° C. Binding studies were conducted both at 37° C. and 20° C., but in this case there was no significant difference. The high binding of HK to most E. coli strains prompted us to test additional E. coli isolates from patients with sepsis and different gastrointestinal infections. High binding of HK was found among enterohaemorrhagic, enterotoxigenic and sepsis strains, whereas enteroinvasive and enteropathogenic strains were negative (FIG. 8). Following growth at 37° C. binding was clearly lower with maximum binding activities around 20 percent. However, the binding pattern was the same.

HK binding strains of E. coli absorb HK from human plasma

To investigate if E. coli bacterial which bind purified HK also take up kininogen from plasma, six strains previously analyzed for binding of radiolabeled HK (strains EHEC 1, EHEC3, EIEC 1, EPEC 1, ETEC5, ES 1 of FIG. 8) were incubated with human plasma for 60 min at 37° C. The bacteria were washed and the plasma proteins bound to the cells were subsequently eluted with pH 2.0. Following centrifugation proteins present in the supernatant were subjected to SDS-PAGE and Western blot analysis (FIG. 8). The monoclonal antibodies used (HKL16) in these experiments detect an epitope in the light chain of HK (see FIG. 2), and as shown in the blot of FIG. 8, the strains that bind radiolabeled HK (EHEC3, ETEC5, ES 1) also absorb HK from human plasma, whereas the non-binding strains (EHEC 1, EIEC 1, EPEC 1) fail to pick up HK from plasma. Due to the qualitative nature of the immunoprint technique, we are unable to assess the fraction of plasma HK absorbed by the bacteria. The bands reacting with the antibodies correspond to single-chain HK (120 kDa), the intact light chain of HK (58 kDa), and a degraded form of the HK light chain (45 kDa). These results demonstrate that E. coli strains binding radiolabeled M also bind HK in a complex mixture of proteins such as plasma (HK represents approximately 0.15% of the total protein content in plasma).

Curli mediate the binding of HK to E. coli

Figure 9:
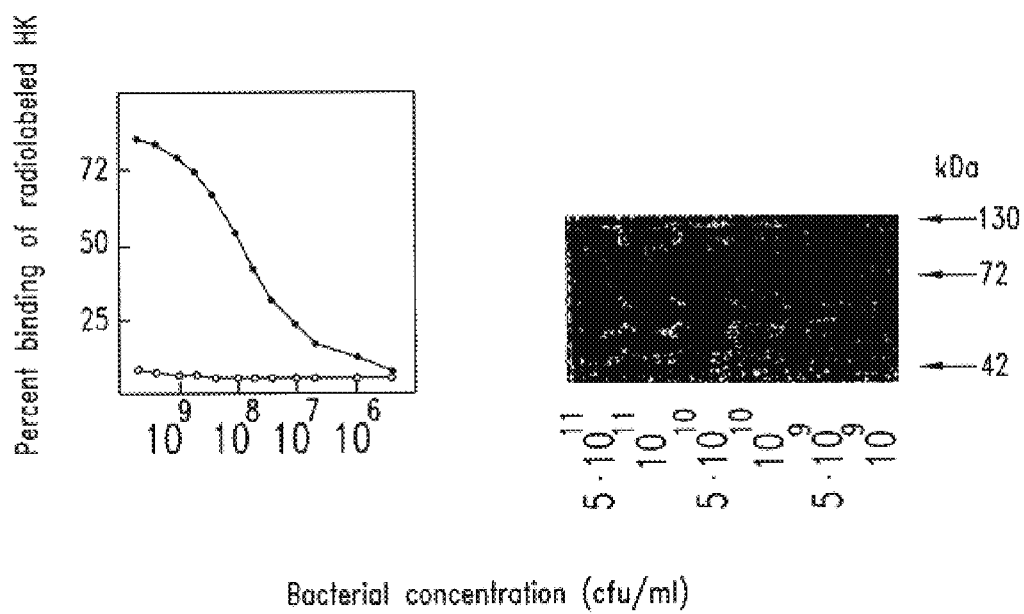
FIG. 9 shows binding of radiolabeled H-kininogen to curli-expressing E. coli. A constant amount of $[^{125}I]$-labeled HK ($10^4$ cpm corresponding to 1 ng in 225 μl) was incubated with different numbers of curliated Ymel (•) or non-curliated Ymel-1 (°)bacteria for 60 min at 37° C. Binding is expressed as the percentage of radioactivity present in the bacterial pellet in relation to the total radioactivity applied per tube (left part of the figure). Increasing numbers of Ymel bacterial were incubated with 1 ml fresh human plasma. Non-curliated Ymel-1 bacteria were added to give $5 \times 10^{11}$ bacteria throughout the tests. Following incubation, proteins bound to the cells were eluted and separated by SDS-PAGE (10%) under reducing conditions, and electrotransferred to a PVDF membrane. The membrane was probed with antibody HKL 16 followed by secondary peroxidase-labeled antibodies (right part of the figure).
Figure 10:
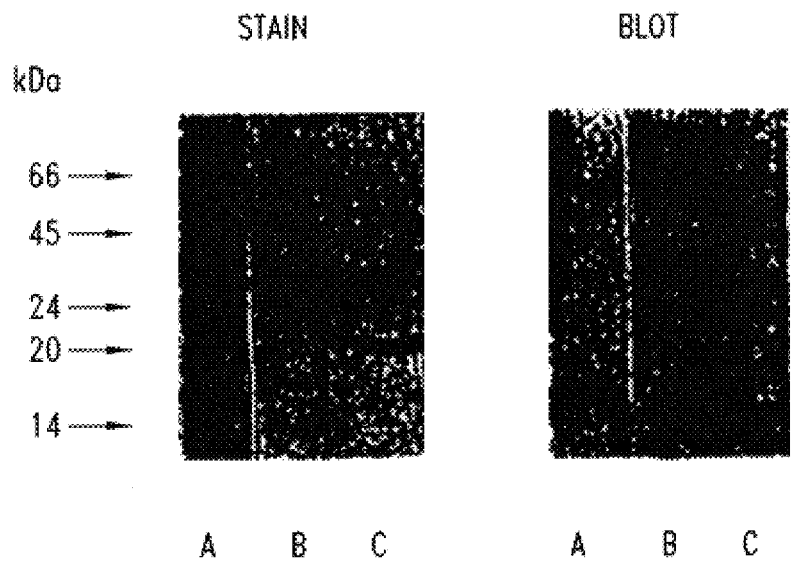
FIG. 10 discloses that H-kininogen binds to purified bacterial protein subunits in Western blots. CurlI subunits purified from Ymel bacteria (A), streptococcal M1 protein (B), and a COOH-terminal fragment thereof, S-C3 (C), were separated by SDS-PAGE (13.6%) under reducing conditions and strained with Coomassie Blue (STRAIN). Proteins were blotted onto PVD17 membranes and probed with $[^{125}I]$-HK (BLOT).
Figure 11:
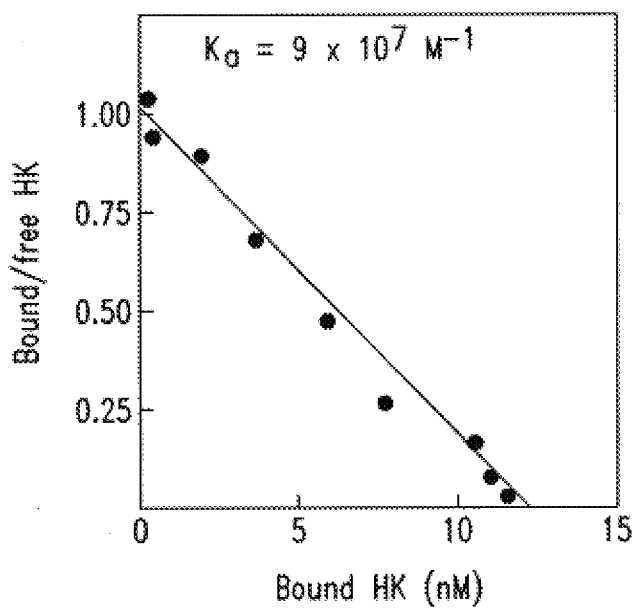
FIG. 11 relates to a Scatchard plot for the binding of H-kininogen to polymeric curli. Constant amounts of polymeric curli and $[^{125}I]$-HK were incubated with varying amounts of unlabeled HK. Free HK was separated from HK bound to curli by centrifugation. The radioactivity of the resulting pellet was measured, and calculation of the affinity constant was done according to Scatchard (1949), The attractions of proteins for small molecule and ions, Ann. N. Y. Acad. Sci. vol. 5 1: pp. 660–672.
Figure 12:
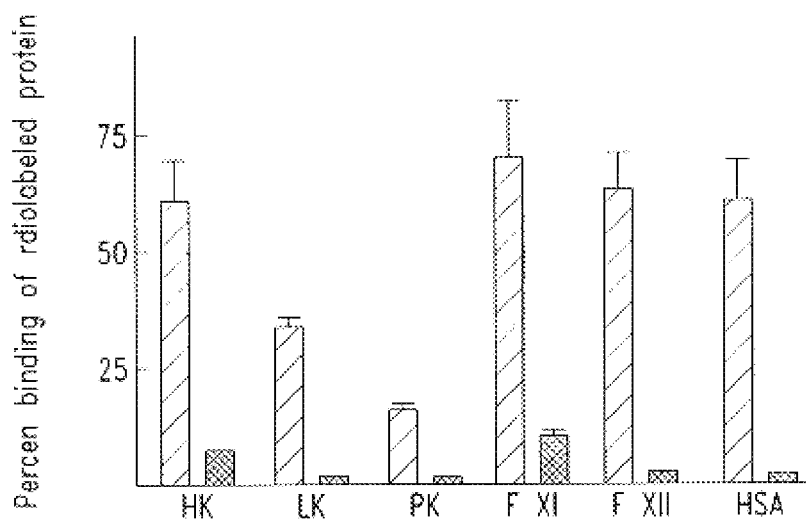
FIG. 12 describes binding of L-kininogen and contact factors to curliated E.coli. $2 \times 10^9$ curli-expressing Ymel (□)

To test whether curli were involved in the binding of the curli-expressing E. coli K12 strain YMel and an isogenic curli deficient mutant strain, YMel-1, were used in binding experiment with [$^{125}$I]-HK. As shown in FIG. 9 (left panel), only curliated Ymel bacteria showed affinity for HK in a concentration-dependent manner. Transcomplementation of the curli-negative YMel-1 strain with a plasmid containing the structural gene for the curli subunit (csgA) restored HK-binding. Plasma absorption experiments performed with different concentrations of YMel bacteria, demonstrated that the amount of HK absorbed by the bacteria was dependent on the number of curliated cells used (FIG. 9, right panel). In these experiments a constant volume of plasma was used, and non-curliated YMel-1 cells were added to give the same total number of bacteria for each absorption experiment. Binding of HK to curli was also demonstrated with purified proteins. Radiolabeled HK was found to bind to monomeric curli subunits directly applied to PVDF membranes (not shown). Curb monomers separated by SDS-PAGE and blotted to PVDF membranes also reacted with [$^{125}$I]-HK (FIG. 10, lane A). In these experiments, intact HK-binding streptococcal M1 protein, and a non-binding COOH-terminal fragment (S-C3) of M1 (Ben Nasr, A., Herwald, H., Muller-Esterl, W., and Bjorck, L. (1995) Human kininogens interact with M protein, a bacterial surface protein and virulence determinant. Biochem J 305: 173–180), were included as positive and negative controls, respectively (FIG. 12, lanes B and C). The immunoprint revealed that M1 protein binds to HK as did curli monomers, but not the S-C3 fragment. Unlabeled HK completely blocked the binding of [$^{125}$I]-labeled HK to curliated E. coli as well as to isolated curli. In Scatchard plots, the affinity constant for the interaction between HK and purified polymeric non-soluble curli was determined to be 9×10$^7$ M$^{-1}$ (FIG. 11). Fibronectin and plasminogen, other ligands for curli (Olsen et al., 1989; Sjobring et al., 1994 op. cit.), only partially blocked the binding of [$^{125}$I]-HK to purified curli (1000 fold molar excess reduced the binding by 20–30%), suggesting that the binding site for HK is separate from those for fibronectin and plasminogen. The presence of large excess of human serum albumin finally, had no effect on the binding of HK to curli (not shown).

Assembly of contact phase factors on curliated E. coli

Figure 2A:
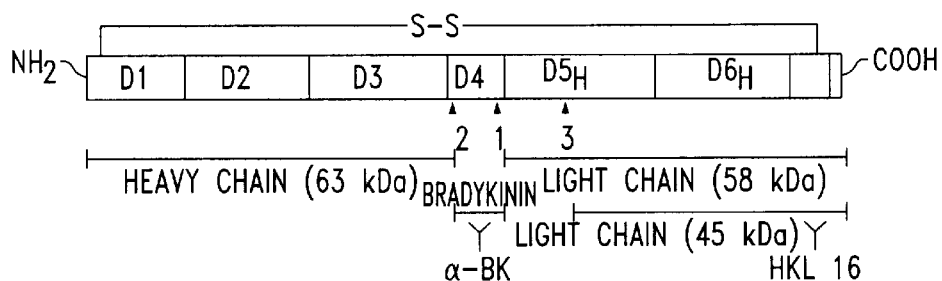
FIG. 2 discloses the structure of H-kininogen and assembly of contact factors. Part A: HK comprises six domains: D 1 to D3 have cystatin-like structure and represent potent cysteine proteinase inhibitors (D2, D3) and expose a cell-binding site (D3). Domain D4 bears the kinin segment. $D5_H$ exposes another cell-binding site, and $D6_H$ holds the zymogen-binding site for prekallikrein and factor XI (shaded). Stepwise proteolysis of HK by α-kallikrein at site 1 (marked by an arrowhead) releases a 63 kDa heavy chain with the bradykinin segment still attached, and a 58 kDa light chain; the two chains are interconnected by a single disulphide bridge. Bradykinin is released following cleaveage at site 2. Secondary cleaveage at site 3 converts the 58 kDa light chain into the 45 kDa light chain fragment. The epitopes of antibodies α-BK and HLK 16 are indicated below the chains. Part B: HK binds to negatively charged surfaces and brings plasma prekallikrein (PK) and factor X(FXI) in proximity to surface-bound factor XII (FXII). Reciprocal proteolytic activation of FXII and PK converts these proenzymes to active proteinase (Henderson et al. 1994, Blood vol. 84, pp 474–482). Activated FXII activates FXI which propagates the intrinsic coagulation pathway via factor IX, whereas activated PK (kallikrein) cleaves HK and releases bradykinin. The triggering event (marked by an asterisk) that starts the contact phase activation is still ill-defined.
Figure 2B:
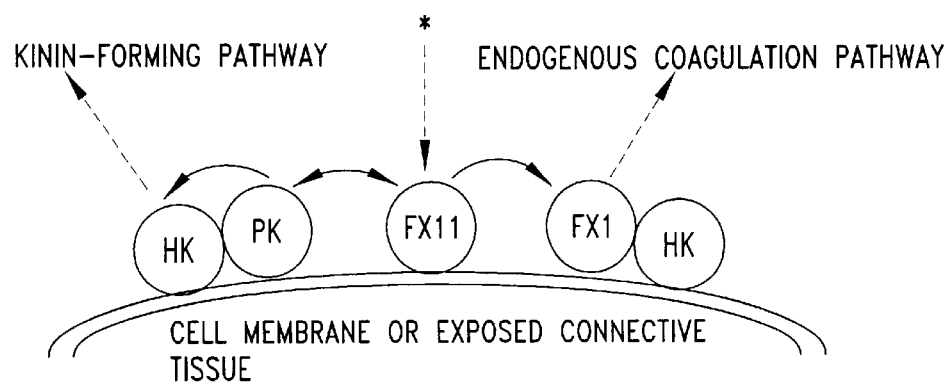

HK is a major constitatent of the contact phase system of the human plasma. Therefore we explored the possibility that other contact factors, i.e. prekallikrein, factor XI and factor XII bind to E. coli. Furthermore we probed for the binding of LK, the low-molecular-weight substrate for kallikrein. Curli-expressing YMel bacteria bound the [$^{125}$I] labeled proteins at 37° C., whereas YMel-1 bacteria failed to show significant binding (FIG. 12). As the control we used [$^{125}$I]-labeled radiolabeled human serum albumin which bound neither to YMel nor to YMel-1 bacteria. The results indicate that the entire set of contact phase factors, i.e. HK, prekallikrein, factors XI and XII, and the kinin precursor LK, may assemble at the surface of curliated bacteria Bradykinin is released from HK bound to curliated E. coli Plasma prekallikrein is activated by factor XII to α, kallikrein, and the proteolytic action of α-kallikrein on HK or LK releases bradykinin. The finding that the various factors are assembled on E. coli prompted us to probe for the kinin present in HK eluted from the bacterial surface. To this end we incubated E. coli bacteria with total human plasma containing the entire set of contact factors. Using antibody HKL16 to the light chain of HK we were able to detect a doublet band of 114–120 kDa under non-reducing conditions (FIG. 13, right panel). An identical replica stained with a polyclonal antibody to bradykinin (A-BK) stained a single band of 120 kDa. Under reducing conditions (FIG. 13, left panel) HKL16 detected three major bands, i.e. single-chain HK of 120 kDa, the intact light chain of 58 kDa, and a degraded form of the light chain of 45 kDa (c.f. FIG. 2). Unlike HKL16, the α-BK antibody decorated two major bands of 120 (single-chain HK) and 64 kDa (heavy chain plus kinin segment) but none of the light chains. Notably (α kallikrein cleaves first at the carboxyterminal flanking site, Arg-Ser, of bradykinin, thereby separating the light chain from the heavy chain which still has bradykinin attached; in a second step kallikrein cleaves at the aminoterminal flanking site, Lys-Arg, thereby releasing the bradykinin peptide from the heavy chain. The cleavage of HK by plasma kallikrein to generate the nonapeptide bradykinin is highly specific (c.f. Silverberg and Kaplan 1988). Together our data indicate that binding of intact HK to the bacterial surface is followed by a (partial) cleavage of HK suggesting that bradykinin might be released from HK under these conditions. It should be pointed out that the degradation of the HK light chain by α-kallikrein is often indicative of the concomitant release of bradykinin from the heavy chain—The plasma sample used for absorption was also incubated without adding bacteria. In this case no degradation of HK was observed (not shown).

To directly follow the release of immunoreactive bradykinin, curliated YMel bacteria were preincubated with fresh human plasma, followed by extensive washing. We then applied α-kallikrein for various time periods, and eluted the surface-bound HK from E. coli. The resultant mixture was analyzed by Western blotting and immunoprinting using the anti-bradykinin antiserum (FIG. 14). After 5 min of incubation, almost all of the 120 kDa (single-chain HK) and most of the 64 kDa band (heavy chain plus bradykinin) had disappeared. At 20 min almost all of the bradykinin immunoreactivity had disappeared, suggesting that bradykinin had been completely liberated. The results clearly indicate a rapid and efficient cleavage of HK under the release of immunoreactive bradykinin.

Discussion

The structural gene for the curli subunit is present in most natural isolates of E. coli, but in vitro curli are expressed preferentially at growth temperatures below 37° C. (Olsen et al., 1989, op. cit). To what extent curli are present on E. coli growing in vivo is not known, but the fact that the level of expression varies considerably among clinical isolates grown at 26° C. (see FIG. 2), indicates that this could be the case also at 37° C. This notion is supported by the finding that some strains of Salmonella express so called thin aggregative fimbriae (Collinson et al., 1991, op.cit.) also when grown at 37° C. (Mikael Relm and Staffan Normark, personal communication). These surface fimbriae are closely related to curli (Collinson et al., 1991, op. cit.; Olsen et al., 1993, op cit). It could also be that curli are present predominantly when E. coli primarily infects and colonizes the human host, or that curli are expressed in vivo under specific environmental conditions. Finally, also a low degree of curli expression could be enough to reach local concentrations of HK and other contact phase factors sufficient to elicit blood coagulation and/or bradykinin release.

Previous work has demonstrated that curli interact with components of the extracellular matrix and the fibrinolytic system (Olsen et al op. cit, 1989; Sjobring et al, 1994, op. cit). The starting point for the present experiment was the binding of HK to various bacterial species, and the subsequent finding that HK in the case of E. coli, binds to curli. An important question raised by the interactions between curli and different host proteins concerns the specificity of a given interaction. Does for instance the binding of HK occur in vivo in the presence of other curli-binding proteins? The fact that M like fibronectin and plasminogen (Olsen et al., 1989, op. cit; Sjobring et al., 1994, op. cit), is bound to curliated E. coli in plasma environment shows that this is the case.

The ability of curli to interact with a variety of host proteins provide the bacteria with adhesive, invasive, and virulence properties. In a first step curli may mediate adherence to cellular and matrix components (Olsen et al, 1989, op. cit). As the infection progresses, the interaction with plasminogen and tissue-type plasminogen activator (tPA) could promote the spreading of the infection by degradation of tissues via activated plasmin (see Parkkinen, L, Hacker, L, and Korhonen, T. & (1991) Enhancement of tissue plasminogen activator catalyzed plasminogen activation by Escherichia coli S fimbriae associated with neonatal septicaemia and meningitis. Thromb Haemost 65: 483–486.; Lottenberg, R-, Minnin-Wenz, D., and Boyl, M. D. P. (1994) Capturing host plasmin(ogen): a common mechanism for invasive pathogens? Trends Microbiol 2: 20–24; Lahteenn-maki K., Virkola, R., Pouttu, R-, Kuusela, P., Kukkonen, M., and Korhonen, T. K. (1995) Bacterial plasminogen receptors: in vitro evidence for a role in degradation of the mammalian extracellular matrix. Infect Immun 63: 3659–3664). In the case of HK the bacteria might exploit the permeability-increasing properties of the cognate effector peptide, bradykinin, in the infectious process. The observation that not only HK, but also other components of the contact phase system bind to curli, suggests that curliated E. coli could act as platforms for the assembly of such components leading to a subsequent activation of the procoagulatory and the proinflammatory pathways. The notion that bacterial endotoxins are potent activators of factor XII (Morrison, D.C., and Cochrane, C. G. (1974) Direct evidence for Hageman factor (factor XII) activation by bacterial lipopolysaccharides (endotoxins). J Exp Med 140: 797–811) which in turn activates prekallikrein and vice versa (FIG. 1) lend further support to our hypothesis. In this way bacteria loaded with the elaborate contact phase activation system might promote the excessive bradykinin release that is not controlled by the otherwise tightly regulated mechanisms of homeostasis. In the case of septicemia a release of bradykinin might produce vasodilation and increase vascular permeability, effects which cause the leakage of plasma, hypovolemic hypotension, and, in severe cases, circulatory shock. Furthermore, the initiation of the intrinsic blood coagulation cascade via surface-bound factor XIa might contribute to hypercoagulability and even to disseminated intravascular coagulation, which represents a serious complication to sepsis. Finally, the acquisition of a surrounding clot could protect the bacteria from the host defense mechanisms.

Microbial pathogenicity and virulence are highly polygenic properties, and the complexity and multitude of molecular interactions creating the host-microbe relationship makes it difficult to predict the effect(s) of a certain interaction. However, if disturbances in the balance between an infecting microorganism and its host causing disease are to be corrected therapeutically, it is necessary to define the molecular interplay which represents the basis for the relationship. The present example describes potential virulence mechanisms which may be used as therapeutic targets, while underlining the complexity of the host-microbe relationship.

Thus, the present invention provides the necessary basis for creating therapeutic agents effective against a wide variety of conditions. One example is Systemic Inflammatory Response Syndrome, previously known as sepsis, septic shock, sepsis syndrome etc, which is caused by inflammatory responses to a variety of stimuli, of which some are infectious in origin (see E. T. Whalley and J. C. Cheronis). According to the present invention, therapeutic agents may be provided, which increase the chances of survival in patients suffering from e.g. this syndrome, even though the underlying etiology is still unknown.

Example 3

Bacterial strains—*S. pyogenes* strains AP 1 (40/58) and AP74 (30/50) are from the World Health Organisation Collaborating Centre for References and Research on Streptococci Institute of Hygiene and Epidemiology, Prague, Czech Republic.

Sources of proteins and antibodies—H-kininogen was isolated from human plasma (Salvesen, G., C. Parkes, M. Abrahamson, A. Grubb, and A. J. Barrett. 1986. Human low-Mr kininogen contains three copies of a cystatin sequence that are divergent in structure and in inhibitory activity for cysteine proteinases. *Biochem. J* 234:429–434 with modifications previously described (Hasan, A. A., D. B. Cines, J. Zhang, and A. H. Schmaier. 1994. The carboxyl terminus of bradykinin and amino terminus of the light chain of kininogens comprise an endothelial cell binding domain—*J. Biol. Chem.* 269:31822–31830). The streptococcal cysteine proteinase (SCP) was purified from the culture medium of strain AP1 (Berge, A., and L. Bjorck. 1995. Streptococcal cysteine proteinase releases biologically active fragments of streptococcal surface proteins. *J Biol. Chem.* 270:9862–9867. The AP1 supernatant was subjected to ammonium sulfate precipitation (80%) followed by fractionation on S-Sepharose in a buffer gradient (5–250 mM MES, pH 6.0). The zymogen was further purified by gel filtration on Sephadex G-200. Monoclonal antibodies to human kininogens (HKH 15 and HKL, 9) were produced in mice (Kaufmann, J., M. Haasemann, S. Modrow, and W. Muller-Esterl. 1993. Structural dissection of the multidomain kininogens. Fine mapping of the target epitopes of antibodies interfering with their functional properties. *J Biol. Chem.* 268:9079–9091.), polyclonal antiserum (AS88) to human H-kininogen in sheep (Muller-Esterl, W., D. Johnson, G. Salvesen, and A. A. Barrett. 1988. Human kininogens. *Methods Enzymol.* 163:240–256), and polyclonal antiserum against the streptococcal cysteine proteinase were raised in rabbits. Antiserum to bradykinin ((x BK, AS348) was produced in a rabbit by previous coupling of the cognate peptides to keyhole limpet hemocyanin (KLH) via the carbodiimide method (Herwald, H., A. H. K. Hasan, J. Godovac-Zimmermann, A. H. Schmaier, and W. Muller-Esterl. 1995. Identification of an endothelial cell binding site on kininogen domain D3. *J Biol. Chem.* 270:14634–14642). Peroxidase-conjugated goat antirabbit goat anti-mouse (Bio-Rad, Richmond, Calif.), or donkey anti-sheep immunoglobumin (ICN, Aurora, Ohio) were used as secondary antibodies. The Z-Leu-Val-Gly-CHN$_2$ peptide has been described (Bjorck, L., P. Akesson, M. Bohus, J. Trojnar, M. Abraham I. Olafsson and A. Grubb. 1989. Bacterial growth blocked by a synthetic peptide based on the structure of a human proteinase inhibitor. *Nature* 337:385–386).

Cleavage off H-kininogen by SCP—H-kininogen (0.5 mg/ml) was incubated at 37° C. with SCP in 10 mM NaH$_2$PO$_4$, 10 mM Na$_2$HPO$_4$, 0.15 M NaCl, pH 7.4 (PBS) containing 1 mM dithiothreitol (DTT); the molar ratio of substrate over enzyme was 100:1 or 1:1. Aliquots (8 µl) of the reaction mixture were removed at the indicated time points, and the reaction stopped by adding 10 µl of a 2% (w/v) sodium dodecyl sulfate (SDS) sample buller (Laemmli, U.K. 1970. Cleavage of structural proteins during the assembly of the head of bacteriophage T4. *Nature* 227:680–685) containing 5% (v/v) 2-mercaptoethanol, and boiling at 95° C. Alternatively the reaction was stopped by addition of 10 µM (final concentration) of [N-(L-3tra nscarboxyoxiran-2-carbonyl)-L-leucyl]-agmatin (E-64).

Cleavage of plasma prekallikrein by SCP—Plasma prekallikrein (16 µg) was incubated with 0.05–0.5 µg of SCP in 100 µl of PBS containing 1 mM DTT at 37° C. for 60 min; the molar ratio was 10:1 to 100:1. The reaction was stopped by adding 10 µl of SDS sample buffer containing 5% 2-mercaptoethanol and boiling at 95° C.; alternatively E-64 was added to a final concentration of 10 µM.

Prekallikrein activation—Plasma prekallikrein (4 µg) was incubated for 1 h with 0.012 µg factor XIIa in 40 µl of PBS, or for 3 h with varying amounts (0.12 to 0.012 µg) of SCP at 37° C. To test the activity of the generated proteinase, kallikrein was added to 200 µl of a 0.6 mM solution of S-2302 (H-D-Pro-Phe-Arg-p-nitro-anilide, Haemochrom, Diagnostica, Essen, Germany) in 0.15 M Tris-HCl, pH 8.3. The substrate hydrolysis was measured at 405 nm.

Cleavage of plasma proteins by SCP—One hundred µl of human plasma was incubated with 3.2 µg of SCP dissolved in 100 µl PBS, 10 mM DTT, pH 7.4, at 37° C. The reaction was stopped by the addition of 100 µl of SDS sample buffer containing 5% 2-mercaptoethanol and boiling at 95° C. for 5 min.

SDS-polyacrylamide gel electrophoresis (PAGE)—Proteins were separated by 10 or 12.5% (w/v) polyacrylamide gel electrophoresis in the presence of 1% (w/v) SDS Standard molecular weight markers were from Sigma.

Western blotting and immunoprinting—Proteins were resolved by SDS-PAGE and transferred onto nitrocellulose membranes for 30 min at 100 mA (Khyse-Andersen, J.1984. Electroblotting of multiple gels: a simple apparatus without buffer tank for rapid transfer of proteins from polyacrylamide to nitrocellulose. *J. Biochem. Biophys. Methods* 10:203–209) The membranes were blocked with 50 mM KH$_2$PO$_4$, 0.2 M NaCl, pH 7.4, containing 5% (w/v) dry milk powder and 0.05% (w/v) Tween 20. Immunoprinting of the transferred proteins was done according to Towbin, H, T. Staehelin, and J. Gordon. (1979. Electrophoretic transfer of proteins from polyacrylamide gels to nitrocellulose sheets: procedure and some applications. *Proc. Natl. Acad Sci. USA* 76:4350–4354). The first antibody was diluted 1:1000 in the blocking buffer (see above). Bound antibody was detected by a peroxidase-conjugated secondary antibody against sheep, rabbit or mouse immunoglobulin followed by the chemiluminescence detection method.

$Ca^{2+}$ release from intracellular stores—Human foreskin fibroblasts (HF-15) on 10 mm diameter glass coverslips were grown to confluency in Dulbecco's modified Eagle's medium supplemented with 10% (v/v) fetal calf serum (Quitterer, U., C Schroder, W. Muller-Esterl, and H. Rehm— 1995. Effects of bradykinin and endothelinl on the calcium homeostasis of mammalian cells. J Biol. Chem. 270:1992–1999). The cells were washed twice with minimum essential medium buffered with 20 mM Na+-HEPES, pH 7.4 (buffer A; without vitamins, and α-D-glucose added immediately before use). The cells were loaded for 30 min at 37° C. with 2 µM 1-[2-(5-carboxyoxazol-2-yl)-6-aminobenzofuran-5-oxy]-2-(2'-amino-5'-methylpheno xy)-ethane-N,N,N',N'-tetra acetic acid, pentaacetoxymethylester (fura2/AM; Calbiochem, San Diego, Calif.) in buffer A containing 0.04% (w/v) of the nonionic detergent pluronic F-127 (Calbiochenl, San Diego, Calif.) (see above). The cells were washed twice with buffer A. The Hitachi F4500 fluorescence photometer was employed with the excitation wavelength alternating between 340 mn and 380 nM and the emission wavelength set at 510 nm. To induce the $Ca^{2+}$ release, 2 µg H-kininogen or proteolytic cleavage products thereof in 20 µl of reaction buffer was added 60 s after starting the measurement. The release of $Ca^{2+}$ from intracellular stores was followed for 300 s; the free intercellular $Ca^{2+}$ concentration was calculated from the ratio of 340 nm/380 nm as described (ses above).

Determination of kinin concentrations in plasma—To measure the SCP-induced kinin release 100 μl of plasma was incubated with 3.2 μg of SCP in 100 μl PBS containing 10 mM DTT. Samples (10 μl each) were removed after 0, 30, 60, 90, and 120 min. The reaction was stopped by adding E-64 to a final concentration of 10 μM. For control 100 μl of human plasma was incubated with buffer in the absence of SCP. The samples were diluted 1:100 in distilled water. Aliquots (100 μl each) were mixed with 20 μl of 20% (w/v) trichloroacetic acid and centrifuged at 1500×g for 10 min. The kinin concentrations in the reaction mixtures were quantitated by the Markit-A kit (Dainippon Pharmaceutical Co., Osaka, Japan) as described (Scott, C. F., E. J. Whitaker, B. F. Hammond, and R-W. Colman. 1993. Purification and characterization of a potent 70-kDa thio lysyl-proteinase (Lys-gingivain) from *Porphyromonas gingivalis* that cleaves kininogens and fibrinogen. *J Biol. Chem.* 268:7935–7942). Briefly, aliquots of the supernatant (75 μl each) were mixed with 75 μl of the kit buffer, and applied to the wells (100 μl each) of microtiter plates that were coated with capture antibodies to rabbit immunoglobulin, followed by specific anti-bradykinin antibodies. After 1 h of incubation, the peroxidase-labelled bradykinin probe was applied and incubated for 1 h. The amount of bound peroxidase was visualised by the substrate solution, 0.1% (w/v) diammonium-2, 2'-azino-bis-(3-ethyl-2,3-dihydrobenzthiazoline)-6-sulfonate (ABTS), 0.012% (v/v) $H_2O_2$ in 100 mM citric acid, 100 mM $NaH_2PO_4$, pH 4.5 for 30 min. The change of absorbance was read at 405 nm. The reference standards were prepared according to the manufacture's instructions.

Animal experiments—*S. pyogenes* of strains API and AP74 were grown in Todd Hewitt broth (Difco, Detroit Mich.) at 37° C. for 16 h, and harvested by centrifugation at 3000×g for 20 min. The bacteria were washed twice with PBS, and resuspended in PBS to $3\times10^8$ cells/ml. One ml of living bacteria was injected intraperitoneally into outbred NMRI mice. Plasma samples were taken 10 h after injection. Alternatively, mice were injected with the purified non-activated SCP (0.1 to 0.5 mg), and plasma samples were taken 60 min, 150 min, and 300 min after injection. For inactivation of SCP, 0.5 mg of the enzyme was mixed with 0.2 mg Z-Leu-Val-Gly-$CHN_2$ prior to injection. To monitor the cleavage of kininogen, 1 μl of plasma was run on SDS-PAGE followed by Western blotting with antibodies against bradykinin (α-BK), *Quantification of SCP in mouse plasma*—One μl of plasma samples from mice injected with SCP was run on SDS-PAGE and transferred onto nitrocellulose. The enzyme was visualized by immunostaining using antibodies against SCP. To obtain semi-quantitative estimates of the SCP amounts in plasma samples, purified SCP (3 ng to 100 ng) was processed as described above and used as a standard.

Results

Streptococcal cysteine proteinase is not inhibited by H-kininogen. The streptococcal cysteine proteinase (SCP) cleaves surfaces proteins of *S. pyogenes* strain AP 1 (see above). One of its target structures, the streptococcal M 1 protein, specifically binds kininogens, (Ben Nasr, A. B., H. Herwald, W. Muller-Esterl, and L. Bjorck. 1995. Human kininogens interact with M protein, a bacterial surface protein and virulence determinant. *Biochem. J* 305:173–180.) the major cycsteine proteinase inhibitors of human plasma. These observations prompted the notion that kininogens bound to the bacterial surface might regulate the proteolytic activity of SCP. We therefore tested the effect of H-kininogen on the hydrolysis of a chromogenic peptide substrate by SCP. Unexpectedly, H-kininogen had no inhibitory effect on the amidolytic activity of SCP (not shown), whereas the synthetic cysteine proteinase inhibitor E-64, efficiently blocked the SCP activity in the same assay. We therefore asked the question whether H-kininogen serves as a substrate—rather than an inhibitor for SCP.

SCP degrades H-kininogen. When we analyzed the reaction mixture of H-kininogen and SCP by SDS-PAGE we found that SCP rapidly and almost completely degraded H-kininogen (FIG. 15). To follow the breakdown of H-kininogen by SCP, and to identify potential cleavage products such as the biologically active kinin peptides, we employed Western blotting and immunoprinting of the reaction mixtures. We used polyclonal antibodies directed to the kinin sequence of 9 residues located in domain D4 of H-kininogen, and monoclonal antibodies to the flanking domains, D3 and D5H (of FIG. 3). FIG. 16 shows three replicas of the SCP cleavage products of H-kininogen separated by SDS-PAGE and immunoprinted by a monoclonal antibody against the COOH-terminal part of domain D3 (HKH 15; FIG. 16A), by a polyclonal antibody to bradykinin (α-BK; FIG. 16B), and by a monoclonal antibody recognizing the $NH_2$-terminal part of domain D5H (HKL 9; FIG. 16C), respectively. The imimmoprints reveal a complex pattern of kininogen degradation products. The native H-kininogen of 105 kDa is rapidly cleaved into fragments of 60 to 75 kDa containing the D3 epitope (panel A), and into fragments of 45 to 70 kDa comprising the D5H epitope (C). Initially the kinin epitope which is rapidly lost from the native kininogen of 105 kDa, remains associated with a band of 60 kDa that is also recognized by the anti-heavy chain antibody (A) but not by the anti-light chain antibody (C). This would indicate that the initial cleavage by SCP occurs at site(s) located distally of the bradykinin moiety, and therefore the bradykinin sequence remains attached to the heavy chain. Further proteolysis by SCP breaks down the kininogen heavy chain, most probably into its constituting domains (note that the various domains D1 through D3 of the kininogen heavy chain are separated by protease-sensitive regions that expose the primary attack sites for many proteinases; (Vogel, R-, I. Assfalg Machleidt A. Esterl, W. Machleidt and W. Muller-Esterl. 1988. Proteinase-sensitive regions in the heavy chain of low molecular weight kininogen map to the inter-domain junctions. *J Biol. Chem.* 263:12661–12668.). Accordingly, a prominent band of approximately 23 kDa appears at the later stages of proteolysis representing domain D3 (B). A fraction of D3 still contains the COOH-terminal extension of bradykinin (B, lanes 3 and 4) that is lost as proteolysis proceeds (120 min). No shift in the apparent molecular mass of the D3 fragment is obvious (see A, lanes 3 to 6) suggesting that only a minor peptide such as bradykinin is removed from the 23 kDa fragment. Nevertheless, we seeked to determine whether SCP releases authentic kinins from H-kininogen.

H-kininogen cleavage products release intracellular Ca2+ in humanfibroblasts. To demonstrate the presence of biologically active kinins in the proteolytic digests we employed the fura-2/AM assay. This test system monitors the bradykinin B2 receptor mediated release of $Ca^{2+}$ from intracellular stores of human foreskin fibroblasts (see above). Purified H-kininogen did not induce a $Ca^{2+}$ release from human fibroblasts 41 (FIG. 17A.); hence the starting product did not contain appreciable amounts of kinins. In contrast the reactions mixtures from the incubation of H-kininogen with SCP for 60 min (C) or 120 min (D) induced significant $Ca^{2+}$ signals thus indicating the presence of biologically active kinins. The specificity of the assay was probed by preincubating the cells with the potent B2 receptor antagonist HOE 140, which completely abrogated the $Ca^{2+}$ signal induced by the application of the kininogen breakdown products (data not shown). H-kininogen which had been incubated for 120 min in the absence of SCP induced no $Ca^{2+}$ signal (data not shown); hence the kinin release was not due to a contaminating kininogenase associated with the starting material. Together these results demonstrate that SCP releases biologically active kinins from H-kininogen.

Figure 1:
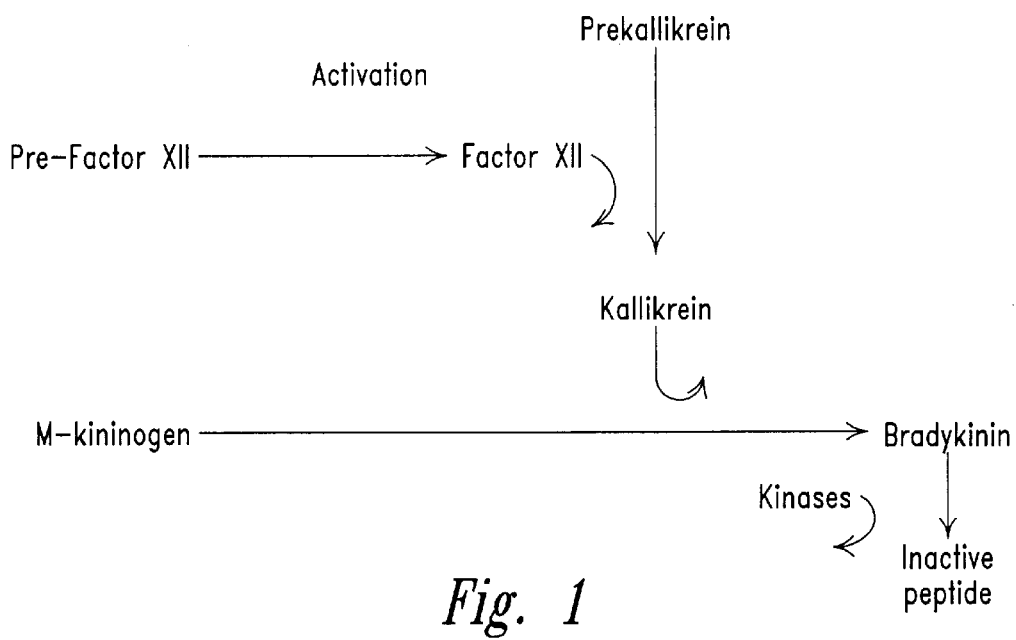
FIG. 1 generally outlines a major route for the formation of bradykinin. Factor XII zymogen is activated either by a part of the clotting cascade, negatively charged surfaces or (disclosed herein) bacterial surface proteins. Activated factor XII then activates prekallikrein thereby forming kallikrein, which in turn cleaves kininogens in order to form bradykinin. Bradykinin has a short half-life and is quickly inactivated by kininase.

SCP cleaves H-kininogen in plasma. To test whether SCP cleaves H-kininogen in its physiological environment the streptococcal enzyme was added to plasma. After varying time points, aliquots were removed from the reaction mixture and subjected to Western blot analyses. Highly specific polyclonal antibodies to native H-kininogen (AS 88) and to bradykinin (α-BK) were applied to identify the kininogen cleavage products in the complex plasma mixture. FIG. 1 SA demonstrates that the endogenous H-kininogen present in human plasma is partially degraded after 15 min, and almost completely split after 30 min of incubation with SCP. Because the antiserum. (AS88) is primarily directed to immunodominant epitopes of the H-kininogen light chain (20) it poorly crossreacts with L-kininogen which is seen as a faint band of 66 kDa (A, lane 1; cf. B, lane 1). The α-BK antibodies reacted weakly with the native forms of H-kininogen and L-kininogen, respectively (B, lane 1). After 15 min of incubation a strong immunoreactivity at 66 kDa is visible which likely corresponds to a kinin-containing fragment representing the kininogen heavy chain including the bradykinin epitope (note that the cleavage of a scissile bond flanking the kinin segment results in a major conformational change of the kininogen molecule and a concomitant exposure of the bradykinin epitope). Under the conditions of our experiment SDS-PAGE does not resolve the putative fragment and L-kininogen because the proteins dilfer only by 36 residues. After 15 min of SCP proteolysis an smaller fragment of approximately 60 kDa is recognized by the anti-bradykinin antibodies (B, lane 2). This latter fragments which peaks at 30 min (B, lane 3) and fades away after prolonged incubation is likely to represent a degradation product of the kinfflogen heavy chain with bradykinin still attached to its carboxyterminus. Unlike the former band, i.e. heavy chain comprising the bradykinin epitope, the latter band, presenting a putative heavy chain degradation product is not observed when kininogen is split by its physiological processing enzyme, plasma kallikrein (see above). The prominent 45 kDa band which occurs throughout the entire incubation procedure (FIG. 18B) is likely to be a staining artefact of the (α-BK antibodies when plasma is used; we did not observe such an immunoreactivity with purified H-kininogen (see FIG. 16). We could not detect any significant kininogen degradation in plasma that was incubated in the absence of SCP (data not shown). Together these data suggest that SCP degrades kininogens both in an isolated system and in complex mixtures such as plasma, and that the rapid loss of kinin immunoreactivity reflects the liberation of the hormone by SCP.

SCP does not activate purified plasma prekallikrein. Under physiological conditions, the kinin release from kininogens is mediated by activated plasma kallilcrein. Due to a reciprocal activation factor XIII converts the zymogen, prekallikrein, to the active enzyme, α-kallikrein. Hence, activation of plasma prekallikrein by SCP may explain at least in part the observed release of kinins, from H-kininogen (see above). To test this possibility, prekallikrein isolated from human plasma was incubated with purified SCP, and followed by SDS-PAGE demonstrating that prekaffihein was rapidly processed by the streptococcal enzyme (data not shown). The resultant cleavage products were tested for their amidolytic activity in chromogenic assays using the pnitroanilide derivative of the tripeptide, H-D-Pro-Phe-Arg. Prekallikrein cleavage products generated by varying concentrations of SCP did not reveal significant amidolytic activity (FIG. 19); likewise prekallikrein or SCP alone had no activity. In contrast prekallikrein activation by factor XIIIa resulted in the progressive activation of the zymogen. Because SCP is unable to activate prekallikrein under the conditions of our experiment we conclude that the bacterial enzyme is likely to act directly on kininogen present in human plasma without prior activation of a physiological kininogenase. This notion is supported by the observation that kininogen degradation products are formed by SCP that do not occur in the krein-mediated processing cascade.

SCP generates kinins from plasma kininogens. Our proteolysis experiments demonstrated that biologically active kinins are released from H-kininogen by SCP in a purified system. We therefore asked the question whether SCP may liberate kinins from kininogens also in a complex environment such as the plasma. To this end we incubated human plasma with purified SCP for 2 h and tested aliquots of the reaction mixture after varying time periods. A competitive ELISA was employed and FIG. 20 demonstrates that SCP release kinins in a time-dependent manner. After 120 min of incubation, the kinin concentration of samples had levelled oll at 2.8 $\mu M$ which almost approaches the theoretically releasable concentration of bradykinin in human plasma of 3.5 $\mu M$. Thus, approximately 0.9 $\mu M$ H-kininogen and 2.6 $\mu M$ L-kininogen are present in human plasma (Mfiller-Esterl, W. 1987. Novel functions of kininogens. *Sem. Thromb. Hemostas.* 13:115–126). No release of kinins was found in controls where plasma was incubated without SCP. These results demonstrate that SCP-induced cleavage of kininogen in plasma is combined with the release of kinin.

SCP cleaves kininogens in vivo. To test whether SCP also processes kininogens in vivo, we injected purified SCP into the peritoneal cavity of mice. Two types of experiments were performed. In the first set of experiments, lethal doses of SCP (0.5 mg per animal) were administrated intraperitoneally, and plasma samples from these animals were taken 60 min, 150 min, and 300 min after injection (FIG. 21A). For control, 0.5 mg SCP that had been inactivated by the specific inhibitor Z-Leu-Val-Gly $CHN_2$ (See above) was injected i.p. into mice, and plasma samples were withdrawn after 300 min. In a second set of experiments, varying amounts of SCP (0.1–0.5 mg) were injected i.p., and plasma samples were taken 300 min thereafter (FIG. 21B). Kininogen degradation in plasma was detected by Western blotting, using antibodies to bradykinin. Three immunoreactive band of 66, 80, and 110 kDa were detected in plasma of mice that had been treated with vehicle only; the upper 110 kDa band and 44 the lower 66 kDa band correspond to H- and L-kininogen, respectively. The intermediate band of 80 kDa may correspond to a modified form of mouse Lkininogen, ir-kininogen, that has recently been described in mouse fibroblasts (Takano, M., K. Yokoyama, K. Yayarna, and H. Okamoto. 1995. Murine fibroblasts synthesize and secrete kininogen in response to cyclic-AMP, prostaglandin E2 and tumor necrosis factor. *Biochim. Biophys. Acta*

1265:189–195). Plasma of mice that had been injected with SCP 60 min prior to bleeding completely lacked the immunoreactive H-kininogen band of 110 kDa. After 150 min most of the plasma kininogens had been degraded, and after 300 min no kinning fragments were detectable. By contrast the majority of plasma kininogens from animals that had been injected with the enzyme-inhibitor complex remained intact.

A dose-dependent effect of SCP on plasma kininogen degradation was found when we injected increasing amounts of SCP (FIG. 21B). Even at lowest enzyme amounts (0.1 and 0.2 mg) a significant fraction of plasma kininogens was found to be degraded. At high SCP amounts 0.4 mg) hardly any kinin-containing kininogen fragments or fragments thereof were detectable. From semi-quantitative Western blot analyses we judged the plasma concentration of SCP to be in the range of 3–25 µg/ml of plasma dependent on the amount of injected enzyme and the time elapsed after injection (Table 2).

Alternatively, living streptococci of strain AP 1 were injected i.p.. Plasma samples were drawn then from the animals 8 h after injection, and analyzed by SDS-PAGE). (FIG. 22). Coomassie Brilliant Blue staining showed no apparent difference between normal mouse plasma and plasma samples from mice injected with SCP or AP 1 bacteria demonstrating that the overall protein composition of plasma was unchanged (FIG. 22A). In the corresponding Western blots, SCP was detected in the plasma of mice given 0.5 mg of the enzyme i.p., but not in the plasma of mice infected with AP 1 bacteria, indicating that the concentration of SCP was lower in the latter experimental setting (data not shown). This observation may also explain why kininogens were not completely degraded in these animals (see FIG. 21B). Immunoprinting of the plasma samples with α-BK antibodies revealed that native H-kininogen was completely absent from the plasma of mice treated with SCP as evidenced by the kinin immunoreactivity. Furthermore, kininogen concentrations were considerably though not completely reduced in the plasma of mice infected with *S. pyogenes* of the AP 1 strain (FIG. 22B). These findings demonstrate that kininogens are also degraded by SCP in vivo, most likely under the release of kinins. For control we used AP 74 bacteria, the only strain of *S. pyogenes* that we have found not to produce SCP (Cooney. Liu, and Bjorck, manuscript in preparation). No significant decrease of kininogens was seen in plasma of mice treated with the same protocol as above except that AP 74 bacteria were used (not shown), thus underlining the specific role for SCP in kininogen turnover and kinin release. Together, these data demonstrate that purified SCP or SCP secreted by *S. pyogenes*, cleaves kininogens in vivo under the release of kinins.

TABLE 2

Quantification of SCP in Mouse Plasma

| Amount of SCOP administered (i.p.) (mg) | Time of the administration (min) | Plasma concentration (µg/ml) |
| --- | --- | --- |
| 0.5 | 60 | 12 |
| 0.5 | 150 | 20 |
| 0.5 | 300 | 25 |
| 0.1 | 300 | 2 |
| 0.2 | 300 | 12 |
| 0.3 | 300 | 12 |
| 0.4 | 300 | 20 |

Example 4

The effects of bradykinin antagonists during bacterial infections were studied in vivousing the *Streptococcus pyogenes* strain AP 1 (Akesson et al., Mol. Immunol., vol 27pp. 523–531) and one of its virulence factors, the streptococcal cysteine proteinase (SCP). In different sets of experiments the bradykinin antagonist HOE 140 (Bao et al. (1991), supra) was injected intraperitoneally or subcutaneously into outbread Nnflu mice. The experiments were designed as follows; mice were injected with lethal doses of SCP intraperitoneally (0.5 mg/animal) or living AP 1 bacteria subcutaneously in an air pocket ($10^7$ bacteria/animal). 5 hours after injecting SCP the mice which received HOE 140 still looked healthy, whereas the mice which did not receive any bradykinin antagonist died. 35 hours after the AP 1 injection the mice who received HOE 140 appeared to be healthy, whereas those who did not appeared to be very ill.

Example 5

Activation of the Contact Phase System on *E. coli* and *Salmonella*

Bacterial strains and culture conditions. YMel is a curli-expressing *E. coli* K12 strain. YMel-1 is an isogenic curli-deficient mutant strain generated by insertional mutagenesis of the csgA gene in YMel. SR11B is a *S. typhimurium* SR-11 X4666 strain; csgA and csgB mutant strains (SR-11 X4666, csgA::Tn1731; SR-11 X4666, csgB::Tn1721) were produced by transposon mutagenesis. Bacteria were grown on colonization factor antigen agar at 37° C. (*S. typhimurium*) or at 26° C. (*E. coli*) and bacteria were washed and resuspended in 50 mM HEPES, 2 mM $CaCl_2$, 50 µM $ZnCl_2$, pH 7.35 containing 0.02% (w/v) $NaN_3$ and 0.05% (v/v) Tween 20 (buffer A). Sources of proteins, HK and PK were isolated from human plasma. F XI and F XII were from Enzyme Research Laboratories (Swansea, UK). Proteins were [$^{125}$] iodinated by the chloramine-T method of Fraker and Speck supra.

Bacterial binding assay. Harvested bacteria were suspended in buffer A to a final count of $2\times10^8$ to $2\times10^{10}$ cell per ml. The bacterial suspension (200 µl) was incubated with radioactively labeled protein at room temperature for 10 to 120 min. Following addition of 2 ml of buffer, the cell suspension was centrifuged, and the radioactivity of the pellet was counted. Binding activity is given as the percentage of bound vs total radioactivity per tube. For electrophoretic analysis, the bacterial pellet was resuspended in 20 µl reducing SDS sample buffer. The samples were boiled at 95° C. followed by centrifugation (3000 g, 5 min) and SDS-PAGE. The mixture of 4 contact-phase factors included $0.2\times10^{-12}$ M F XI, $3.0\times10^{-12}$ M F XII, $3.0\times10^{-12}$ M PK and $4.6\times10^{-12}$ M HK (final concentrations). For autoradiography gels were dried and exposed to Kodak Scientific Imaging Film for 1 to 4 days (Eastman Kodak, Rochester, N.Y.).

Bradykinin determination. Human plasma samples (0.5 ml each ) were incubated with 0.5 ml bacteria ($2\times10^{10}$ bacteria/ml). Following incubation the bacteria were recovered and washed as detailed above. Pellets were resuspended in 0.5 ml buffer A. After a 15 min incubation at room temperature, the bacteria were centrifuged at 3000 g for 5 min. The supernatants were acidified with an equal volume of 0.1% (v/v) trifluoroacetuc acid, and applied to a SEP-Pak Light C18 cartridge (Waters Corp., Milford, Mass.) pre-equilibrated with the same buffer. The column was washed with 6.0 ml 60% (v/v) acetonitrile in 0.1% trifluoroacetic acid. Fractions were lyophilized and redissolved in 250 µl RIA buffer (Bradykinin radioimmunoassay kit; Peninsula Laboratories, Belmont, Calif.), and their bradykinin concentration was determined following the manufacturer's instructions.

Clotting assay. The clotting time was measured in a coagulometer (Amelung, Lemgo, Germany). A bacterial suspension ($6 \times 10^4$ cells/30 µl of 50 mM HEPES, 50 µM $ZnCl_2$, pH 7.35) was incubated with 100 µl of sodium citrate-treated normal human plasma for 30 s, followed by incubation with Platelin LS (aPTT kit; Organon Teknica, Durham, N.C.) or phospholipids only (37.5% phosphatidyl choline, 37.5% phosphatidyl ethanolamino and 35% phosphatidyl serine, all were obtained from Sigma Chemical (St. Louis, Mo.). To initiate clotting 100 µl of 25 mM $CaCl_2$ was added.

Scanning electron microscopy. Clots were gently drawn down onto a Millipore filter (Waters Corp) by suction caused by a wet filter paper lying underneath. The filters were fixed in 2% (v/v) glutaraldehyde, 0.1 M cacodylate, 0.1 M sucrose, pH 7.2 for 1 h at 4° C., and washed with 0.15 M cacodylate, pH 7.2. The filters were postfixed for 1 h with 1% (w/v) osmium tetroxide, 0.15 M sodium cacodylate, pH 7.2 for 1 h at 4° C., washed and stored in cacodylate buffer. Fixed filter paper samples were dehydrated with an ascending ethanol series (10 min per each step), dried, mounted on aluminium holders, sputtered with palladium/gold and examined in a Jeol JSM-350 scanning electron microscope (Jeol, Chicago, Ill.).

Plasma protein concentrations following absorption with bacteria. Bacteria ($2 \times 10^{10}$/ml) in 0.11 M sodium citrate, pH 7.35, were incubated for 15 min with an equal volume of sodium citrate-treated human plasma, followed by centrifugation 5 min at 3000 g. F XI and F XII (human and mouse) were both measured with clotting-based assays using the aPTT reaction (activated partial thromboplastin time) and human deficiency plasma. Protein C was measured with Coatest protein C kit form Chromogenix (Protac-Agkistrodon Contortrix) and AS-2366 (Chromogenix AB, Molndal, Sweden). The concentration of remaining plasma proteins in the supernatant were determined. Mouse fibrinogen was determined by a modified Schneider test.

Animal experiments. Female outbred NMRI mice were given an intravenous injection of 0.5 ml of vehicle or bacterial suspensions ($2 \times 10^{10}$ cells/ml) in 0.1 M phosphate, 0.15 M NaCl, pH 7.4; three animals were used in each group. Blood was collected 15 min or 60 min after injection by intracardiac puncture.

Binding of contact-phase proteins to curliated bacteria. Initially we tested the binding of the human contact-phase proteins F XI, F XII, PK and HK to curliated *Escherichia coli* (strain Ymel) and *Salmonella typhimurium* (strain SR11B) bacteria. As a control, one isogenic *E. coli* mutant strain (strain Ymel-1) and two *S. typhimurium* mutant strains (strains CsgA and CsgB), all lacking curli expression were used. Curliated bacteria, but not curli-deficient mutant strains, avidly bound the various radiolabelled contact factors (FIG. 23) demonstrating that the curli proteins play a crucial role in contact factor binding.

Limited proteolysis of the contact factors indicates the activation of the corresponding pathway. Radiolabelled contact phase factors that had been isolated from human plasma were individually incubated with curliated bacteria for 10 to 45 min. Samples were drawn, and the absorbed proteins were eluted from bacteria and analysed by SDS polyacrylamide gel electrophoresis (SDS-PAGE) followed by autoradiography. Upon incubation with bacteria, F XII was readily cleaved into two major products of 30 and 50 kDa (FIG. 24A) which likely correspond to the heavy and light chain of F XIIa respectively. In contrast HK, PK and F XI remained intact (data not shown).

Figure 24B:
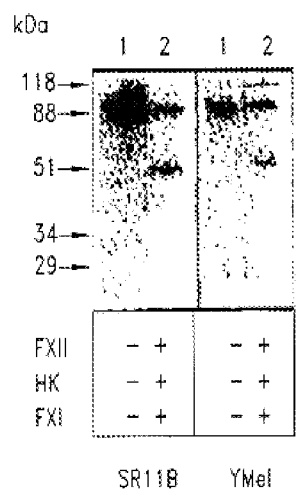
Figure 24C:
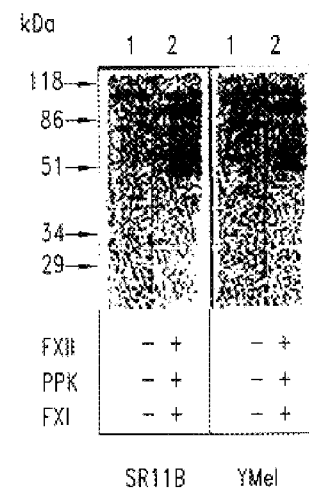

The interaction of contact factors with bacterial surfaces was further analyzed by incubating curliated strains SR11B and Ymel with a mixture of the four contact factors that reflected their molar ratios in human plasma. Only one factor was radiolabeled in each experiment. Incubation of $^{125}$I-labeled PK in the presence but not in the absence of F XI, F XII and HK resulted in the typical cleavage pattern indicative of PK activation (FIG. 24B). Likewise $^{125}$I-labeled HK was cleaved into its heavy and light chains of 65 and 66 kDa, respectively (FIG. 24C) when the mixture of contact factors was present, suggesting that kinin was released. In contrast, no such activation occurred when the mixture of contact factors was incubated in the absence of bacteria (data not shown). These results that the contact-phase system is activated upon exposure to bacteria surfaces and that the initial step is likely to be F XII activation.

Interactions in plasma environment.

Figure 25A:
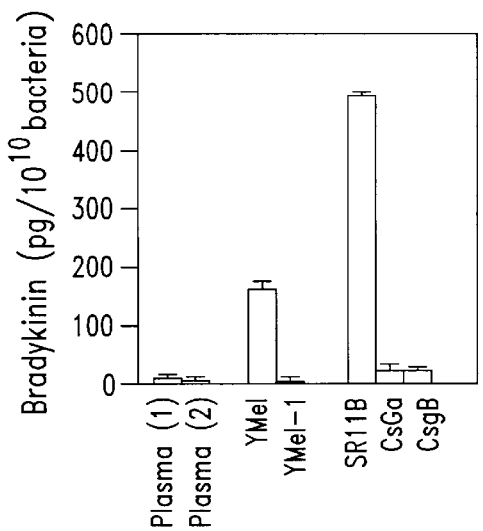
Figure 25B:
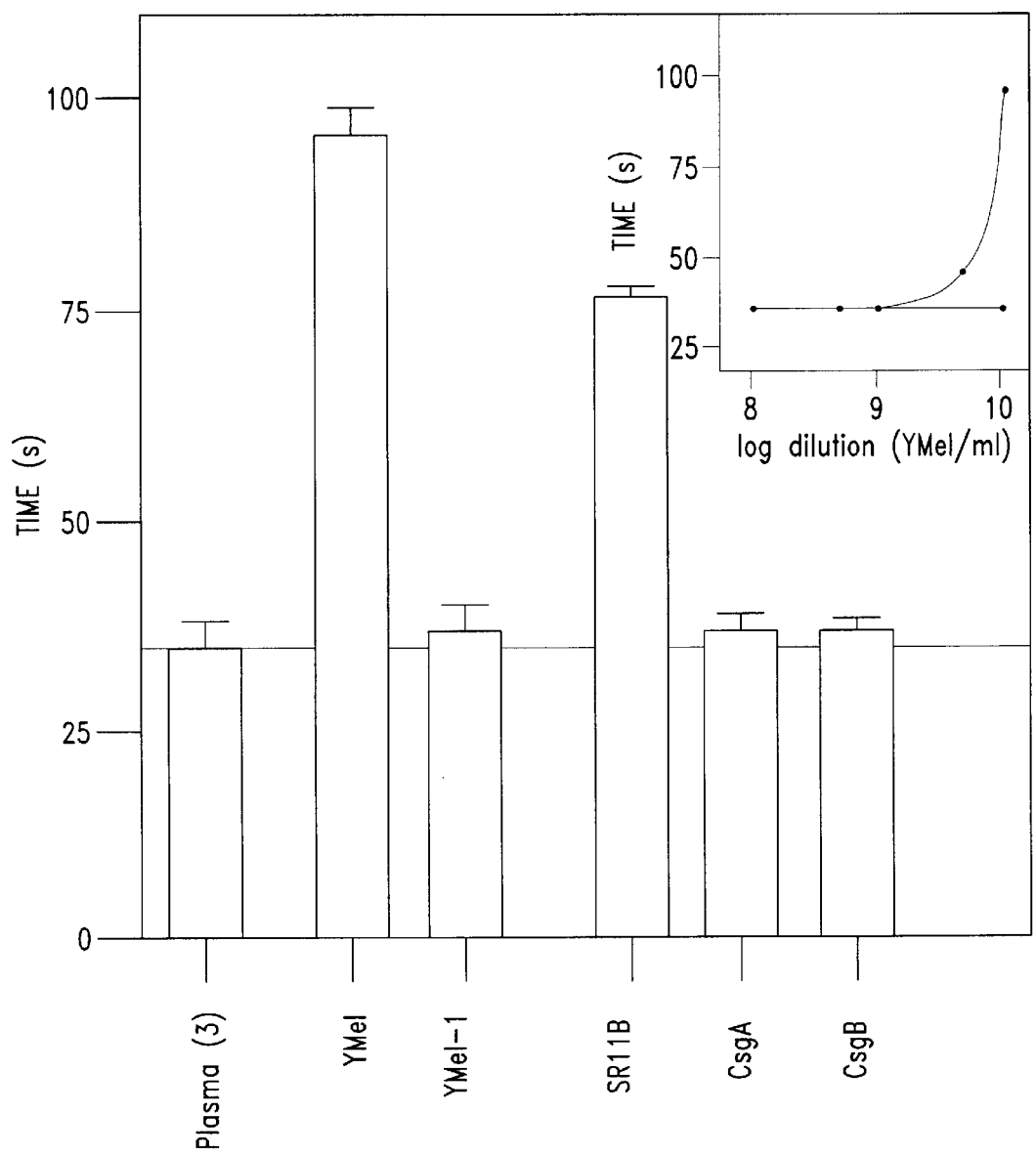

The curliated Ymel and SR11B strains were incubated with whole human plasma; the curli-defiant isogenic mutant strains YMel-1, CsgA and CsgB served as the controls. Proteins bound to the bacteria were solubilized, separated and subjected to Western blot analysis. F XI, F XII, PK and HK were absorbed from plasma by the curliated bacteria, but not by the mutant strains (data not shown). Furthermore, proteolytic activity of F XIa, F XIIa and PKa was associated with Ymel and SR11B bacteria, as demonstrated by chromogenic substrate assays; no such activity was detectable in noncurliated strains (data not shown). To monitor the initiation of the contact-phase system on bacterial surfaces, we examined the release of bradykinin by radioimmunoassay following incubation of plasma for 10 minutes with curliated or noncurliated strains. Incubation of plasma alone served as the control (FIG. 25A). Coincubation with curliated bacteria SR11B and YMel resulted in a dramatic increase of bradykinin release (100- and 30-fold, respectively, over control), whereas noncurliated strains YMel-1, CsgA and CsgB liberated only minor amounts of kinins. Collectively, these data show that curliated bacteria have the capacity to absorb contact-phase factors from plasma, to activate the contact-phase system and to release bradykinin from kininogen.

Curliated bacteria prolong the clotting time.

In another series of experiments, we studied the effect of curliated bacteria on clot formation by measuring the activated partial thromboplastic time (aPTT). Addition of curliated strains YMel and SR11B to plasma drastically prolonged the clotting time (FIG. 25b), whereas mutants YMel-1, CsgA and CsgB were without effect. The effect of YMel on the aPTT was dose-dependent (FIG. 25B) as was that of SR11B (data not shown). Physical separation of the bacteria from plasma before performing the apTT assay did not influence the clotting time (data not shown).

Prolonged clot formation is typically caused by a deficiency or defect of coagulation factors. Thus, the plasma samples were incubated with various bacterial strains, and following centrifugation the concentrations of selected coagulation factors were determined in the supernatants (Table 31). There was no significant consumption of factor X, protein C or antithrombin III. F XI concentrations were slightly reduced following preincubation with YMel and SR11B but not with YMel-1, CsgA or CsgB. However, the concentrations of fibrinogen were significantly lower in plasma preabsorbed with YMel and SR11B, and almost unaffected in plasma exposed to the mutants. The most pronounced effect was seen for the F XII concentration, which dramatically dropped upon incubation with curliated bacteria (Table 3). Hence, curliated bacteria deplete F XII and other coagulation factors such as fibrinogen, thereby prolonging the clotting time.

TABLE 3

Concentration of coagulation factors in human plasma following absorption with different bacterial strains

| Strain | Factor X* (%) | Factor XI* (%) | Factor XII* (g/l) | Fibrogen (IU/ml) | Protein C (IU/ml) | ATT III (IU/ml) |
|---|---|---|---|---|---|---|
| YMel | 58 | 38 | 5 | <0.8 | 0.68 | 0.56 |
| YMel-1 | 71 | 48 | 48 | 1.65 | 0.58 | 0.56 |
| SR11B | 64 | 37 | 6 | <0.8 | 0.71 | 0.58 |
| CsgA | 58 | 61 | 45 | 1.62 | 0.6 | 0.58 |
| CsgB | 60 | 66 | 44 | 1.9 | 0.56 | 0.57 |
| Plasma | 71 | 59 | 58 | 1.62 | 0.58 | 0.54 |

*The concentration was expressed as a percentage of the activity of the factors in pooled normal human plasma Electron microscopic analysis of clots.

Clots were induced in plasma, in the presence or absence of bacteria, and analyzed by scanning electron microscopy. Clot formation in the absence of bacteria resulted in long, polymerized fibrin fibrils. Presence of YMel and SR11B bacteria dramatically changed clot morphology: incorporation of bacteria into the clot resulted in a reduced length and diameter of the fibrin fibrils and in a disturbance of the fibrin network, whereas noncurliated mutants had little effect on the network morphology. These results suggest that the depletion of contact-phase proteins and clotting factors by curliated bacteria and their incorporation into the fibrin network disturbs clot formation, prolongs the clotting time, and changes fibril morphology.

To test their effects in animals, the curliated strains YMel and SR11B, as well as the mutant strains YMel-1 and CsgA, were injected intravenously into mice; vehicle alone served as the control. Blood samples were drawn 15 minutes after injection, clots were allowed to form and were analyzed by electron microscopy. In the absence of bacteria, the clots mainly consisted of erythrocytes that were crosslinked by an extensive fibrin network. The general organisation of the fibrin network, that is the length and diameter of the fibers, was reminiscent of that formed by normal plasma. In contrast, clots from mice injected with curliated YMel and SR11B were almost devoid of a fibrin network, whereas clots from control animals infected with noncurliated YMel-1 and CsgB had a normal architecture.

Curliated bacteria induce a hypocoagulatory state in vivo

Figure 26A:
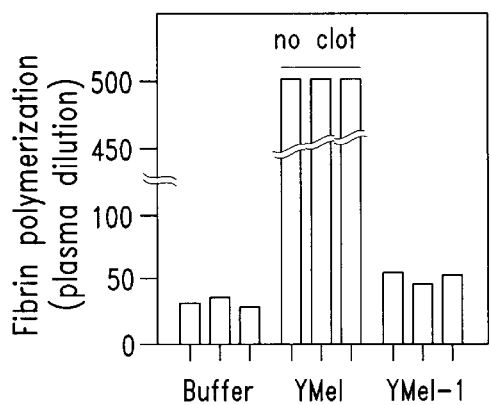
Figure 26B:
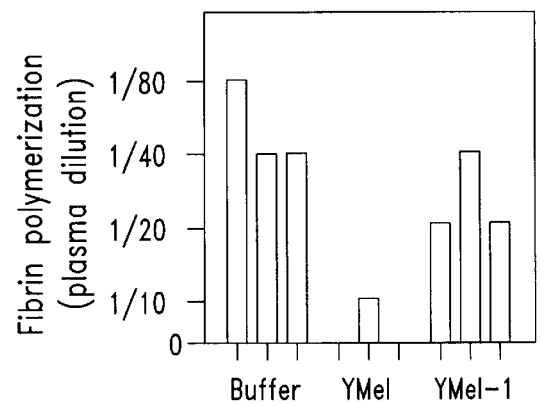

Determinations of the clotting time (aPTT) of plasma samples from mice infected with the E. coli strains Ymel and YMel-1 were in line with these observations. Thus, no clots were formed in samples from mice infected with curliated YMel bacteria even 500 seconds after initiation of the coagulation cascase (FIG. 26A), which corresponded to an almost complete depletion of fibrinogen in the samples as measured by a semiquantitative method (FIG. 26B). The clotting time and fibrinogen level of plasma samples from mice infected with noncurliated YMel-1 bacteria were only slightly affected as compared with those of samples from mice given vehicle alone (FIGS. 26A and B). These in vivo data are fully compatible with the in vitro results and demonstrate that experimental infections with curliated bacteria cause blocking of the intrinsic pathway of coagulation and disturbance of fibrin polymerization through fibrinogen depletion.

Example 6

Activation of the contact phase system by streptococci

Bacteria strains and culture conditions—S. pyogenes strains AP1 (40/58) of the M1 serotype and AP6 (2/66) of the M6 serotype are from the World Health Organisation Collaborating Centre for References and Research on Streptococci, Institute of Hygiene and Epidemionlogy, Prague, Czech Republic. Streptococci, grown in Todd-Hewitt (Difco) at 37° C. for 16 h were harvested by centrifugation (2000 g, 20 min), washed in 50 mM HEPES, 2 mM, $CaCl_2$, 50 µM $ZnCl_2$, pH 7.35 containing 0.02% (w/v) $NaN_3$ and 0.05% (v/v) Tween 20 (buffer A), and resuspended in buffer A.

Sources of proteins—HK and PK were isolated from plasma, F XI and F XII were from Enzyme Research Laboratories, Swansea, UK. Polyclonal antisera against HK were produced in sheep, antisera against PK in rabbits. Antibodies against human F XII were from The Binding Site Limited, Birmingham, UK, and antisera against human F XI were from Nordic Immunological Laboratories, Tilburg, The Netherlands. Peroxidase-conjugated goat anti-rabbit IgG (Bio-Rad, Richmond, Calif.), and donkey anti-sheep IgG (ICN, Aurora, Ohio) were used as secondary antibodies. Proteins were iodinated by the Chloramin-T method of Fraker and Speck, Biochem Biophys. Res. Commun 1978 80 840–857.

Bacterial binding assay—Bacteria were resuspended in buffer A to $2 \times 10^8$ cells per ml. 200 µl of the bacterial solution was incubated with the radiolabelled protein ($2 \times 10^4 - 4 \times 10^4$ cpm) in 25 µl buffer A, at room temperature for 10 to 120 min. After incubation and washing, the pellet was resuspended in 20 µl SDS-PAGE sample buffer containing 1% (v/v) Nonidet P-40 (NP-40) and β-mercaptoethanol. The samples were boiled for 5 min followed by centrifugation (3000×g, 5 min) and SDS-PAGE. The four contact phase proteins were also added together to the bacteria. The following concentrations were used: $3.0 \times 10^{-12}$ M F XII, $3.9 \times 10^{-12}$ M PK, $0.2 \times 10^{-12}$ M F XI and $4.6 \times 10^{-12}$ M HK. In each experiment one of the four proteins was radiolabelled. Following incubation, bacteria were treated as above. Radioactivity released from bacteria was analysed by autoradiography. Dried gels were exposed on Kodak Scientific Imaging Film for one to four days.

SDS-polyacrylamide gel electrophoresis (PAGE) and Western blotting—Proteins were separated by SDS-PAGE, visualised by autoradiography or transferred onto nitrocellulose membranes for 30 min at 100 mA. The membranes were blocked with 50 mM $KH_2PO_4$, 0.2 M NaCl, pH 7.4, containing 5% (w/v) dry milk powder and 0.05% (v/v) Tween 20. Immunoprinting of the transferred proteins was done. The first antibody was diluted 1:1000 in the same buffer as described above. Bopund antibody was detected by a peroxidase conjugated secondary antibody against sheep or rabbit IgG identified by the chemiluminescence method.

Absorption experiments—Plasma absorption experiments were performed. One ml fresh human plasma was incubated with bacteria ($2 \times 10^{10}$ bacterial cells/ml) suspended in 1.0 ml buffer A for 60 min at room temperature. After centrifugation (3000×g for 5 min), the cells were washed three times with 1.5 ml of buffer A and absorbed proteins were eluted with 0.2 ml 30 mM HCl, pH 2.0. The bacteria were centrifugated and the supernatant was neutralised with 20 µl 1 M Tris, pH 8.0, 0.2 ml SDS-sample buffer was added and the mixture was boiled for 5 min. Eluted proteins were analysed by SDS-PAGE and Western blotting using antibodies against HK, F XII, F XI or PK.

Analysis of proteolytic activity at bacterial surface—0.5 ml plasma including proteinase inhibitors (10 mM Pefabloc, Roth, Karlsruhe, Germany; 10 mM PMSF, Sigma Chem Co, St. Louis, Mo., 10 mM Benzamidine, Sigma Chem, Co, St.

Louis, Mo.) were incubated with $2 \times 10^{10}$ cells/ml in 0.5 ml buffer A for 10 min at room temperature. The bacteria were centrifuged and washed three times in buffer A. To measure the proteolytic activities, the bacteria were resuspended in 0.25 ml of a 0.6 mM solution or S-2302 (H-D-Pro-Phe-Arg-pNA:2HCl) or S-2366 (H-D-Glu-Pro-Arg-pNA:2HCl; Haemochrom Diagnostica, Essen, Germany) in 0.15 M Tris-HCl, pH 8.3. After 30 min the bacteria were centifuged and substrate hydrolysis in the supernatant was measured at 405 nm.

Clotting assay—The clotting time was monitored in an Amelung coagulometer (Amelung, Lemgo, Germany). 30 μl of a solution of $2 \times 10^{10}$ bacteria resolved in 100 μl of a 50 mM HEPES, 50 μM $ZnCl_2$, pH 7.35 solution were incubated with sodium citrate-treated plasma for 30 s, followed by incubation with Platelin® LS aPTT (Organon Teknica, Durham, N.C.) or with phospholipids alone (37.5% phosphatidyl choline, 37.5% phospatidylethanolamine and 25% phosphatidyl serine; all from Sigma Chem. Co, St. Louis, Mo.) for 200 s. Coagulation was initiated by adding 100 μl of a 25 mM $CaCl_2$ solution.

Scanning electron microscopy—For scanning electron microscopy (SEM), the clots were gently drawn down onto a wet Millipore filter (Waters Corporation, Milford, Mass.) by suction caused by presetted filter paper lying underneath. Subsequently the whole filter was fixed in 2% (v/v) glutaraldehyde in 0.1 M sodium cacodylate plus 0.1 M sucrose, pH 7.2, for 1 h at 4° C. and the washed with 0.15 M cacodylate buffer, pH 7.2. The filters were then washed with cacodylate buffer, and postfixed for 1 h in 1% (w/v) osmium tetroxide in 0.15 M sodium cacodylate, pH 7.2 for 1 h at 4° C., washed, and stored in cacodylate buffer. Fixed filter paper sample were dehydrated for 10 min at each step of an ascending ethanol series, critical point dried, mounted on aluminium holders, palladium/gold sputtered, and examined in a Jeol JSM-350 SEM.

S. pyogenes of strain AP1 was grown as described above. The bacteria were washed twice with sterile PBS, and resuspended in sterile PBS to a concentration of $2 \times 10^{10}$ cells/ml in the absence or presence of 0.2 mg/ml of F XII inhibitor H-D-Pro-Phe-Arg-CMK (Bachem, Switzerland). Female outbred NMRI mice were given an intravenous injection of 200 μl vehicle or 200 μl bacterial suspension, during ether anaesthesia. 15 min following the injection, the animals were again anaesthetized and blood samples were taken by punction of the heart. Animals were killed by cervical dislocation.

Assembly of contact phase proteins on streptococcal surface structures—In order to study the influence of streptococci on the intrinsic pathway of coagulation, binding of all contact phase proteins to the streptococcal serotypes AP1 and AP6 was investigated. In direct binding assays we found, that radio-labelled contact phase factors are absorbed on the surfaces on the strains AP1 and AP6 (data not shown), whereas the Gram-negative strain CsgA which does not express curli from Salmonella typhimurium failed to show a significant binding. We incubated the radio-labelled proteins with AP1 and AP6 bacteria and analysed absorbed proteins by SDS-PAGE. Only F XII was degraded resulting in two fragments of 50 kDa and 30 kDa, respectively. In this context it is noteworthy to mention, that limited proteolysis is the general mechanism of converting coagulation factors to their active forms. Since the F XII fragments on the streptococcal surfaces correspond to heavy and light chain of the active enzyme, the results indicate that the molecule is activated upon binding to streptococci. However, no degradation of HK, PK and F XI was detected and F XII was not cleaved when incubated in the absence of bacteria under the same conditions (data not shown).

The interaction between F XII and the other members of the contact phase system was analysed by incubating bacteria with all four proteins together, whereby the molar ratios of the coagulation factors were the same as in plasma and only one protein was radioactively labelled. Radiolabelled PK was only cleaved in the presence of F XII, HK and F XI when incubated with bacteria. No degradation of PK was monitored in the absence of these factors. In analogue experiments, radio-labelled HK was also only cleaved in the presence of all four factors when applied to the bacteria (FIG. 27). The resulting HK fragments of 65 kDa and 55 kDa correspond to heavy and light chain of kinin-free HK. Under identical conditions but in the absence of bacteria no degradation of radio-labelled contact phase factors was observed (data not shown). Taken together these results indicate that the binding of contact phase factors to the streptococcal surfaces initiate the contact phase system via initial activation of F XII.

Contact phase proteins are captured from plasma by streptococci—In another series of experiments we investigated the interaction between bacteria and contact phase proteins under physiological conditions, in that the streptococcal strains AP1 and AP6 were incubated with human plasma. After extensive washing, absorbed proteins were eluted from the bacterial surface and run on SDS-PAGE followed by transfer on nitrocellulose. Separated proteins were probed by antibodies against F XII, HK, PK and F XI. As a control, the non-binding strain CsgA was used. AP1 and AP6 captured all four contact phase proteins from plasma whereas CsgA failed to show significant binding. Interestingly, the proteins were degraded. These finding support the notion that the contact phase system is also triggered under physiological conditions.

The amidolytic activity of the streptococcal absorbed factors was studied in chromogenic assays. The proteolytic assay was established such that bacteria were incubated with plasma and, after an extensive washing procedure, they were resuspended in a buffer containing the specific substrates for F XI, H-D-Glu-Pro-Arg-pNA (S-2366), and for F XII/PK, H-D-Pro-Phe-Arg-pNA (S-2302). To this end proteolytic activities of the F XI and F XII/PK were found on the surfaces of AP1 and AP6, whereas the activities observed on the surface of control strain CsgA were significantly reduced (FIG. 28). When we tested the endogenous activities on bacterial surfaces, none of these strains was able to hydrolyse any of the substrates in the absence of plasma (data not shown). The findings described above are in accordance with our previous reported data showing that streptococcal bound HK releases bradykinin by PK treatment. Thus, the experiments demonstrated, that after streptococcal contact with plasma the bacteria are able to assembly all four coagulation factors followed by activation of the contact phase system.

Figure 29C:
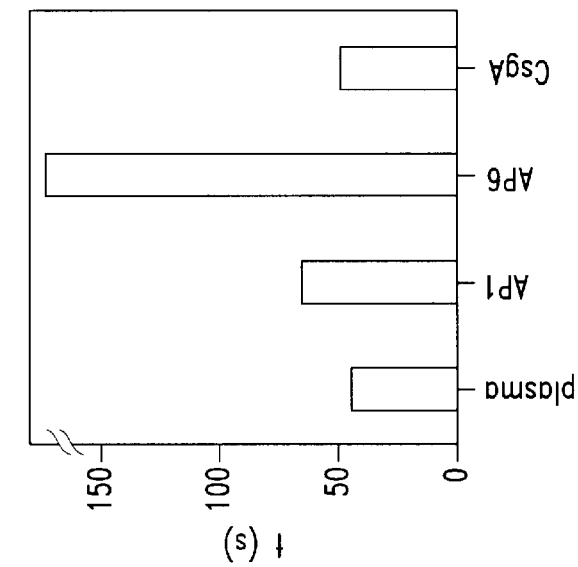
Figure 29B:
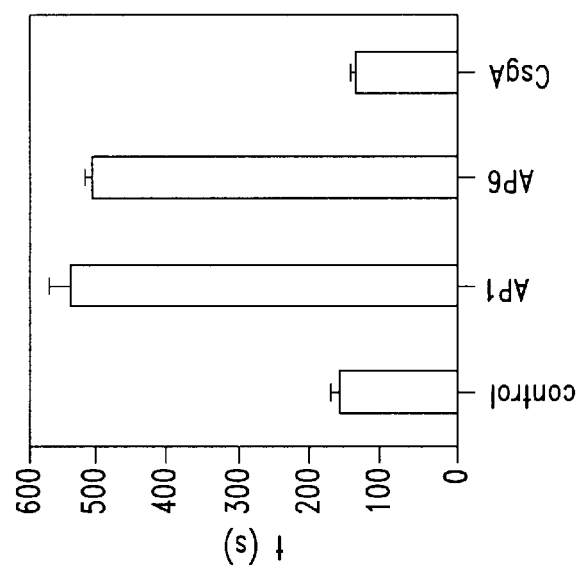
Figure 29A:
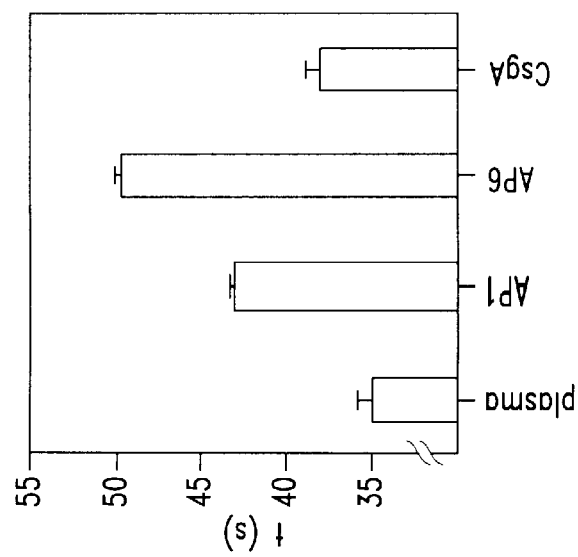

Influence of streptococci on the clotting time—To test the influence of streptococci on clot-formation we employed the kaolin activated partial thromboplastin time (aPTT) assay. In these experiments, plasma was pre-incubated with bacteria followed by measurements of the resulting aPTT values. As shown in FIG. 29A, AP1 and AP6 significantly prolonged the clot-formation as compared to plasma in absence of bacteria. The control strain CsgA had only a small effect on the APTT. Similar results were obtained for the clotting time in the absence of kaolin (FIG. 29B), These results were unexpected wince the activation of the contact phase system should initiate the coagulation system. However, prolongation of clot formation occurs normally by deficiency of coagulation factors in plasma.

We tested if a consumption of coagulation factors by the bacteria was responsible for the observed effect. The experiments were constructed such that plasma and bacteria were incubated for 30 min followed by removing bacteria from plasma by centrifugation. The resulting supernatants were used for the determination of the kaolin activated aPTT. As observed before, pre-incubation of plasma with AP1 and AP6 prolonged the clot-formation whereas the CsgA failed to induce a delay in the same set-up (FIG. 29C). These data suggest, that not the presence of bacteria but a consumption of coagulation factors induced this effect. Analysis of the plasma-supernatants after incubation with bacteria revealed, that fibrinogen was almost completely depleted when plasma was pre-incubated with AP1 and AP6. No fibrinogen depletion was observed in samples treated with CsgA in the same experiment (data not shown). Finally, these measurements demonstrated that, despite the initiation of the contact phase system on streptococcal surfaces, consumption of fibrinogen and probably other coagulation factors induced a disturbance in clot formation.

Electron microscopic studies of clots formed from plasma in the presence of bacteria. In further studies morphological alternations of clots in presence of streptococci were investigated. Clots formed from human plasma in the absence of kaolin with and without bacteria were analysed by electron microscopy. As shown in figure, control clots without bacteria are built by long, thick fibrin polymers forming a fibrin network. In presence of AP1 and AP6 no fibrin network formation was detectable and bacteria were inserted into the clots. In contrast, clots formed in the presence of CsgA bacteria showed a normal fibrin network formation as observed in the control clot and no bacteria were inserted into the clot. Taken together these results imply that the ability of streptococci to bind to and to activate contact phase proteins on their surfaces results in a prolongation of the clotting time, a change in fibrin fibril morphology and an incorporation of bacteria inside the clots.

To study the interaction between streptococci and the contact phase system in vivo an animal model was established. In these experiments, mice were intravenously injected with AP1 and AP6 and alternatively with the same bacteria in the presence of the F XII inhibitor H-D-Pro-Phe-Arg-CMK. As a control vehicle along was applied. A short time after injection blood samples were taken from the animals and clots were formed, which were in addition analysed by electron microscopy. Clots created in the absence of streptococci were built by arythrocytes cross linked via a fibrin network. However, when AP1 and AP6 were injected into the animals clots were formed by densely packed erythrocytes in the absence of a fibrin network and bacteria were incorporated in the clots. When bacteria were injected together with the F XII inhibitor, clots appeared as observed in the control resulting in precipitated erythrocytes cross linked via a fibrin network and no bacteria were incorporated in the clots. From the electron-micrographs it can be concluded that the presence of streptococci in the bloodstream induces dysfunctions in clot-formation and that inhibition of F XII activity abolished this effect. Thus, in conclusion, these data demonstrated that the activation of the contact phase system during streptococcal infection is combined with a change in the coagulation properties of the host.

What is claimed is:

1. An assay for compounds useful in the treatment of bacterial induced coagulation disorders, comprising:
    (a) incubating a plasma sample with a strain of bacteria;
    (b) adding a compound to be assayed to the plasma sample before, during or after step (a);
    (c) conducting an activated partial thromboplastin time test after steps (a) and (b); and
    (d) determining the clotting time;
wherein a decrease in clotting time indicates a compound useful in the treatment of bacterial induced coagulation disorders.

2. The assay according to claim 1 in which the bacteria are removed from the sample prior to step (b) or step (c).

3. An assay for compounds useful in the treatment of bacterial induced coagulation or inflammatory disorders, comprising:
    (a) incubating a sample of bacteria with one or more contact phase proteins selected from the group consisting of H-kininogen, prekallikrein, factor XII and factor XI;
    (b) adding a compound to be assayed before, during or after step (a); and
    (c) determining the binding of the contact phase proteins to the bacterial surface;
wherein a decrease in the binding of said contact phase proteins to said bacterial surface indicates a compound useful in the treatment of bacterial induced coagulation and/or inflammatory disorders.

4. An assay for compounds useful in the treatment of bacterial induced coagulation or inflammatory disorders, comprising:
    (a) incubating a strain of bacteria with one or more contact phase proteins selected from the group consisting of H-kininogen, prekallikrein, factor XII and factor XI;
    (b) adding the compound to be assayed before, during or after step (a); and
    (c) determining the activation of the or each contact phase protein;
wherein a decrease in the activation of the contact phase protein or each contact phase protein indicates that said compound is useful in the treatment of a bacterial induced coagulation and/or inflammatory disorder.

5. The assay according to claim 4 wherein H-kininogen is present in the sample and activation is monitored by release of bradykinin.

* * * * *

UNITED STATES PATENT AND TRADEMARK OFFICE
CERTIFICATE OF CORRECTION

PATENT NO. : 6,242,210 B1
DATED : June 5, 2001
INVENTOR(S) : Lars Björck et al.

It is certified that error appears in the above-identified patent and that said Letters Patent is hereby corrected as shown below:

<u>Column 40, claim 4,</u>
Line 49, "activation of the contact phase" should read -- activation of the or each contact phase --.
Line 50, "protein or each contact phase protein indicates that said" should read -- protein indicates that said --.

Signed and Sealed this

Ninth Day of April, 2002

Attest:

JAMES E. ROGAN
Attesting Officer         Director of the United States Patent and Trademark Office